US008465940B2

(12) United States Patent
Umegae et al.

(10) Patent No.: US 8,465,940 B2
(45) Date of Patent: Jun. 18, 2013

(54) METHOD FOR ELECTROCHEMICALLY MEASURING 1,5-ANHYDROGLUCITOL IN WHOLE BLOOD

(75) Inventors: Yoshihiko Umegae, Takasaki (JP); Reiko Machida, Takasaki (JP); Hisako Takagi, Takasaki (JP); Yayoi Irie, Takasaki (JP); Takao Yokoyama, Takasaki (JP); Toshio Tanabe, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 341 days.

(21) Appl. No.: 12/448,120

(22) PCT Filed: Dec. 13, 2007

(86) PCT No.: PCT/JP2007/074047
§ 371 (c)(1),
(2), (4) Date: Jun. 9, 2009

(87) PCT Pub. No.: WO2008/072702
PCT Pub. Date: Jun. 19, 2008

(65) Prior Publication Data
US 2010/0062469 A1 Mar. 11, 2010

(30) Foreign Application Priority Data
Dec. 14, 2006 (JP) ................................. 2006-336789

(51) Int. Cl.
C12Q 1/54 (2006.01)

(52) U.S. Cl.
USPC ............................................. 435/14; 435/25

(58) Field of Classification Search
USPC .................................................... 435/14, 25
See application file for complete search history.

(56) References Cited

U.S. PATENT DOCUMENTS

| | | | |
|---|---|---|---|
| 4,810,640 A | 3/1989 | Nakamura et al. | |
| 4,916,069 A | 4/1990 | Fujiwara et al. | |
| 4,994,377 A | 2/1991 | Nakamura et al. | |
| 5,374,546 A | 12/1994 | Nagel et al. | |
| 5,407,806 A | 4/1995 | Yabuuchi et al. | |
| 5,426,033 A | 6/1995 | Kojima et al. | |
| 5,821,073 A | 10/1998 | Lee | |
| 5,871,949 A | 2/1999 | Ebinuma et al. | |
| 6,268,166 B1 | 7/2001 | Kojima et al. | |
| 6,448,029 B1 | 9/2002 | Tazoe et al. | |
| 6,541,215 B1 | 4/2003 | Ebinuma et al. | |
| 6,764,581 B1 | 7/2004 | Forrow et al. | |
| 2002/0027072 A1 | 3/2002 | Cui et al. | |
| 2004/0053349 A1* | 3/2004 | Citri | 435/7.32 |
| 2010/0075352 A1* | 3/2010 | Umegae et al. | 435/14 |
| 2011/0031118 A1* | 2/2011 | Machida et al. | 204/403.14 |
| 2011/0165608 A1* | 7/2011 | Machida et al. | 435/28 |

FOREIGN PATENT DOCUMENTS

| | | |
|---|---|---|
| CN | 1257128 A | 6/2000 |
| EP | 0159727 A2 | 10/1985 |
| EP | 0436897 A2 | 7/1991 |
| JP | 62-79780 | 4/1987 |
| JP | 63-22185 | 1/1988 |
| JP | 63-185397 | 7/1988 |
| JP | 2-268679 | 11/1990 |
| JP | 3-27299 A | 2/1991 |
| JP | 4-212060 A | 8/1992 |
| JP | 5-76397 A | 3/1993 |
| JP | 5-223773 | 8/1993 |
| JP | 5-304997 | 11/1993 |
| JP | 7-67697 | 3/1995 |
| JP | 7-36756 A | 4/1995 |
| JP | 8-70893 * | 3/1996 |
| JP | 8-298996 A | 11/1996 |
| JP | 10-10125 A | 1/1998 |
| JP | 10-62402 | 3/1998 |
| JP | 10-179140 | 7/1998 |
| JP | 10-191998 | 7/1998 |
| JP | 11-18760 | 1/1999 |
| JP | 2872983 | 1/1999 |
| JP | 2983015 | 9/1999 |
| JP | 2000-135079 | 5/2000 |
| JP | 2000-175698 | 6/2000 |
| JP | 2001-78797 | 3/2001 |
| JP | 3170320 | 3/2001 |
| JP | 2001-116756 | 4/2001 |

(Continued)

OTHER PUBLICATIONS

McGill J. et al. Circulating 1,5AG Levels in Adult Patients with Diabetes Reflect Longitudinal Changes of Glycemia. Diabetes Care 27(8)1859-1865, 2004.*
BioMedical Chromatography, vol. 7, 41-44 (1993); Shigeru Tajima et al.; "Determination of 1,5-Anhydroglucitol in Urine by High Performance Liquid Chromatography and an Enzyme Sensor"—XP002556865.
Clinica Chimica Acta 350 (2004) 201-209; William Nowatzke et al.; "Evaluation of an assay for serum 1,5-anhydroglucitol (GlycoMark™) and determination of reference intervals on the Hitachi 917 analyzer"—XP004629829.

(Continued)

Primary Examiner — Ralph Gitomer
(74) Attorney, Agent, or Firm — Nields, Lemack & Frame, LLC

(57) ABSTRACT

By a method for measuring 1,5-anhydroglucitol, comprising the steps of: eliminating or converting glucose interfering with the measurement of 1,5-anhydroglucitol and/or a derivative thereof beforehand; and measuring 1,5-anhydroglucitol performed thereafter, wherein such glucose and/or a derivative thereof are/is eliminated or converted in whole blood as such without performing blood cell separation, an enzyme for measuring 1,5-anhydroglucitol is allowed to act on without performing blood cell separation, and 1,5-anhydroglucitol is electrochemically measured, it becomes possible to measure 1,5-anhydroglucitol using a small amount of whole blood without resort to a centrifuge or the like. Accordingly, this measurement method can be applied to rapid measurement of 1,5-anhydroglucitol at bedside or in a medical examination room or to home self-measurement thereof by a patient.

12 Claims, 18 Drawing Sheets

FOREIGN PATENT DOCUMENTS

| | | |
|---|---|---|
| JP | 2001-133430 A | 5/2001 |
| JP | 2001-190299 A | 7/2001 |
| JP | 2001-197900 A | 7/2001 |
| JP | 3217180 | 8/2001 |
| JP | 2002-90331 A | 3/2002 |
| JP | 2002-514744 | 5/2002 |
| JP | 2003-83958 A | 3/2003 |
| JP | 2005-523443 | 8/2005 |
| JP | 3713049 | 8/2005 |
| JP | 2006-275819 | 10/2006 |
| WO | 96/25514 A1 | 8/1996 |
| WO | 02/33407 A1 | 4/2002 |
| WO | 2006/134870 | 12/2006 |

OTHER PUBLICATIONS

The European communication dated Dec. 4, 2009.
Clinical Chemistry, vol. 40, No. 11 (1994), pp. 2013-2016 "Fully Enzymatic Method for Determining 1,5-Anhydro-D-glucitol in Serum", XP002478498, Fukumura, et al.
Clinical Chemistry, vol. 47, No. 10 (2001), pp. 1829-1835, "Microvolume Blood-Sampling Device with Low Hemolysis and High Consistent Yield of Serum Components", Tanaka, et al.
European Communication dated May 30, 2008 in co-pending foreign applications EP 06757237 and PCT/JP2006311752/ co-pending U.S. Appl. No. 11/921,917.
International Search Report dated Jul. 18, 2006 in co-pending foreign application No. PCT/JP/2006/311752/co-pending U.S. Appl. No. 11/921,917.
Office Action dated Sep. 29, 2010 in co-pending U.S. Appl. No. 11/921,917.
Office Action dated Dec. 21, 2010 in co-pending U.S. Appl. No. 11/921,917.
Chinese Communication, with English translation, dated May 31, 2011 in co-pending foreign patent application No. CN 200680028932.0 (document serial No. 2011052600534800).
Denki Kagaku, vol. 63, No. 10. p. 907-911 (1995).
BioMedical Chromatography, vol. 7, 41-44 (1993); Shigeru Tajima et al.; "Determination of 1,5-Anhydroglucitol in Urine by High Performance Liquid Chromatography and an Enzyme Sensor".
The International Search Report dated Mar. 25, 2008.
Final Rejection dated Jun. 1, 2011 in co-pending U.S. Appl. No. 11/921,017.
Office Action dated Oct. 25, 2011 in co-pending U.S. Appl. No. 11/921,917.
Final Rejection mailed Mar. 13, 2012 in co-pending U.S. Appl. No. 11/921,917.
Merck Manual Home Edition, Section: Hormonal and Metabolic Disorders, Chapter: "Diabetes Mellitus", 12 pages, last full review/revision in Jun. 2008 by Preeti Kishore, MD, accessed Aug. 19, 2012 @ http://www.merckmanuals.com/home/print/hormonal_and_metabolic_disorders/diabetes_mellitus.
Kimball's Biology Pages (online biology textbook), "Transport Across Cell Membranes", 10 pages, Feb. 5, 2011, by John W. Kimball, accessed Aug. 19, 2012 @ http://users.rcn.com/jkimball.ma.ultranet/Biology/Pages/D/diffusion.html.
Biochimica et Biophysica Acta, vol. 255, 1972, pp. 126-132, "Kinetic Parameters of Glucose Efflux From Human Red Blood Cells Under Zero-Trans Conditions", Karlish, et al.
Diabetes Care, vol. 4, No. 5, Sep.-Oct. 1981, pp. 551-555, "Glycosylated Hemoglobin in Relation to Rapid Fluctuations in Blood Glucose in Children with Insulin-dependent Diabetes: A Comparison of Methods With and Without Prior Dialysis", Ditzel, et al.
Clinical Chemistry, vol. 35, No. 2, 1989, pp. 315-317, "Effectiveness of Sodium Fluoride as a Preservative of Glucose in Blood", Chan, et al.
Chinese Communication, with English translation, dated Dec. 28, 2012 in corresponding Chinese Patent Application No. 200780046209.X.
Japanese Communication mailed Jul. 13, 2012 in corresponding Japanese Patent Application No. 2008-549361.

* cited by examiner

METHOD FOR ELECTROCHEMICALLY MEASURING 1,5-ANHYDROGLUCITOL IN WHOLE BLOOD

This application is a National Stage US Application filed under Rule 371 based upon PCT/JP2007/074047 filed Dec. 13, 2007.

TECHNICAL FIELD

The present invention relates to a method for measuring 1,5-anhydroglucitol in blood that is subject to interference by glucose and/or a derivative thereof, specifically, a method for electrochemically measuring 1,5-anhydroglucitol in blood, characterized in that whole blood is used as a specimen, and blood cell separation is not required, a sensor chip used for the measurement, and a kit for measuring 1,5-anhydroglucitol including the sensor chip.

BACKGROUND ART

In recent years, the number of diabetic patients has been increasing as the diet has become richer. To prevent complications in diabetic patients, blood sugar levels need to be maintained at the levels close to those of healthy individuals, and apparatus for self-measurement of blood sugar levels are widely used so that patients can monitor the blood sugar levels themselves at home. However, since blood sugar levels vary depending on the meal, and the measurement has to be done frequently, patients suffer from a heavy burden. It is also difficult for patients to correctly interpret measured values due to lack of knowledge, and it is not easy to strictly control blood sugar levels.

Meanwhile, since 1,5-anhydroglucitol is not affected by meal and reflect the blood sugar control in diabetic patients over the past one week, diabetic patients can correctly understand their blood sugar control by "once weekly" measurement at home alone. A 1,5-anhydroglucitol self-measurement kit would provide a great advantage for patients, but conventional methods for measuring 1,5-anhydroglucitol using serum or plasma as a specimen require blood cell separation and are not suitable for self-measurement because the measurement requires a large amount of a specimen. Therefore, 1,5-anhydroglucitol self-measurement kits, including those using a trace amount of whole blood as it is as a specimen, have not been realized.

The 1,5-anhydroglucitol measuring methods described in PATENT DOCUMENTS 1 to 9 use serum or plasma as a specimen, not whole blood, and do not involve electrochemical measurement.

Furthermore, when a whole blood specimen is used for the 1,5 AG Kit for Animals (Nippon Kayaku Co., Ltd.) distributed by Wako Pure Chemical Industries, Ltd., blood is hemolysed by adding purified water or an aqueous solution of 10 mM ethylenediamine tetraacetic acid (EDTA) and further centrifuged, the supernatant is treated with a column, and 1,5-anhydroglucitol is measured by a colorimetric method using a pigment. In other words, this method is not a method for electrochemically measuring 1,5-anhydroglucitol using whole blood as it is as a specimen without separating blood cells.

The reason for conventionally using serum or plasma as a specimen, not whole blood, is that glucose is also contained in blood cells. Even when a reagent for eliminating or converting glucose is added to whole blood, glucose remains in blood cells without being eliminated or converted. Since glucose is released through the cell membrane in the step of measuring 1,5-anhydroglucitol in blood, interference by glucose cannot be completely eliminated. In a reaction for detecting 1,5-anhydroglucitol in blood, interference by hemoglobin in erythrocytes having an oxidation-reduction ability is expected. So far, a method for measuring blood 1,5-anhydroglucitol using whole blood by enzymatically eliminating or converting glucose beforehand without separating blood cells is not known.

Furthermore, methods for electrochemically measuring 1,5-anhydroglucitol are described in NON-PATENT DOCUMENT 1 and PATENT DOCUMENTS 10 and 11. However, NON-PATENT DOCUMENT 1 describes a method for measuring 1,5-anhydroglucitol in urine using an enzyme sensor composed of a hydrogen peroxide electrode and an enzyme-fixed membrane. However, measurement of 1,5-anhydroglucitol in whole blood, in which glucose and the like coexist, is not mentioned. In PATENT DOCUMENT 10, 1,5-anhydroglucitol is measured by amperometry using a dehydrogenase and phenazine methosulfate as an electron acceptor. However, only examples for the reference standard of 1,5-anhydroglucitol are mentioned, and there is no description about the measurement in whole blood. In PATENT DOCUMENT 11, an enzyme having an ability of oxidizing 1,5-anhydroglucitol is allowed to act, and the produced hydrogen peroxide is electrochemically measured using a hydrogen peroxide electrode. However, serum is used in this measurement as well, and this is not a measurement method using whole blood.

Meanwhile, 1,5-anhydroglucitol is a compound which is a reduced glucose at the position of 1 and has a chemical structure very similar to that of glucose. Therefore, many of enzymes used for measurement of 1,5-anhydroglucitol also react with glucose. Blood contains glucose 20 times or more abundant than 1,5-anhydroglucitol. Therefore, to measure 1,5-anhydroglucitol, glucose must be eliminated or converted in some way so that glucose should not react with enzymes for measuring 1,5-anhydroglucitol. Furthermore, when glucose derivatives produced by this conversion react with enzymes for measuring 1,5-anhydroglucitol, these derivatives must also be eliminated or converted.

Glucose is eliminated or converted by oxidizing glucose with glucose oxidase or phosphorylating glucose with hexokinase in PATENT DOCUMENT 1, oxidizing glucose with glucose oxidase and gluconolactonase or glucose dehydrogenase and gluconolactonase in PATENT DOCUMENT 2, converting glucose to fructose-1,6-diphosphate with hexokinase, phosphohexose isomerase, and 6-phosphofructokinase or glucose isomerase, fructokinase, and 6-phosphofructokinase in PATENT DOCUMENTS 3 and 4, phosphorylating glucose with glucokinase or hexokinase in PATENT DOCUMENT 5, and phosphorylating glucose with an enzyme that phosphorylates glucose to glucose-6-phosphate in PATENT DOCUMENT 6, and then 1,5-anhydroglucitol is measured. In these documents, glucose is converted to glucono-1,5-lactone, glucose-6-phosphate, gluconic acid, fructose-6-phosphate, fructose-1,6-diphosphate, or the like. So far, however, measurement by eliminating or converting glucose in whole blood with an enzyme and then quantifying electrochemically 1,5-anhydroglucitol in whole blood with an enzyme is not known.

PATENT DOCUMENT 1: Japanese Patent No. 2983015
PATENT DOCUMENT 2: JP-A-2001-78797
PATENT DOCUMENT 3: Japanese Patent No. 3170320
PATENT DOCUMENT 4: Japanese Patent No. 3217180
PATENT DOCUMENT 5: JP-A-2001-116756
PATENT DOCUMENT 6: Japanese Patent No. 2872983
PATENT DOCUMENT 7: JP-A-63-185397
PATENT DOCUMENT 8: JP-A-10-191998
PATENT DOCUMENT 9: JP-A-8-70893

PATENT DOCUMENT 10: JP-A-7-67697
PATENT DOCUMENT 11: JP-A-62-79780
PATENT DOCUMENT 12: JP-A-5-304997
PATENT DOCUMENT 13: JP-A-63-22185
PATENT DOCUMENT 14: JP-A-2-268679
PATENT DOCUMENT 15: JP-A-2000-135079
PATENT DOCUMENT 16: JP-A-11-18760
PATENT DOCUMENT 17: JP-A-2000-175698
PATENT DOCUMENT 18: JP-A-10-179140
NON-PATENT DOCUMENT 1: Biomed. Chromatogr., vol. 7, p. 41 (1993)

DISCLOSURE OF THE INVENTION

Problems to be Solved by the Invention

For clinical laboratory testing, recently, rapidly measurement of various test items at bedside or in a clinic called Point of Care Testing and measurement of blood sugar levels by patients themselves at home have been increasingly implemented. Since use of a centrifuge or the like in such cases for obtaining serum or plasma is complicated and requires time, use at actual clinical setting is difficult. In particular, in the measurement by patients themselves at home, a trace amount, such as not more than several tens μL of blood collected using a lancet device and a sample collecting device is used as a sample. Therefore, measurement methods using a centrifuge to obtain serum cannot be employed. Thus, a method for measuring 1,5-anhydroglucitol using whole blood as it is as a specimen has been awaited.

Means for Solving the Problems

The inventors of the present invention conducted various research in order to solve the foregoing problems. As a result, they found a method for electrochemically measuring 1,5-anhydroglucitol in blood using whole blood as it is as a specimen, and accomplished the present invention.

That is, the present invention relates to the followings.

(1) A method for measuring 1,5-anhydroglucitol in whole blood, comprising the step of eliminating or converting glucose and/or a derivative thereof that interferes with the measurement and the subsequent step of measuring 1,5-anhydroglucitol, wherein whole blood is used as it is without separating blood cells by eliminating or converting glucose and/or a derivative thereof, and an enzyme for measuring 1,5-anhydroglucitol is further allowed to act without separating blood cells to electrochemically measure 1,5-anhydroglucitol.

(2) The method for measuring 1,5-anhydroglucitol according to the above (1), wherein the enzyme for measuring 1,5-anhydroglucitol is an oxidoreductase.

(3) The method for measuring 1,5-anhydroglucitol according to the above (2), wherein the oxidoreductase is pyranose oxidase, L-sorbose oxidase, or 1,5-anhydroglucitol dehydrogenase.

(4) The method for measuring 1,5-anhydroglucitol according to the above (3), wherein the oxidoreductase is derived from the genus *Pseudomonas* or *Agrobacterium*.

(5) The method for measuring 1,5-anhydroglucitol according to any one of the above (1) to (4), wherein the 1,5-anhydroglucitol is electrochemically measured in the presence of a redox mediator.

(6) The method for measuring 1,5-anhydroglucitol according to the above (5), wherein the redox mediator is an osmium complex, a quinone compound, a ferrocene compound, a phenothiazine compound, a phenoxazine compound, a phenazine compound, an indophenol compound, a diphenylamine compound, or a phenol compound.

(7) The method for measuring 1,5-anhydroglucitol according to any one of the above (1) to (6), wherein the glucose and/or a derivative thereof is eliminated or converted with an enzyme from whole blood as it is without separating blood cells.

(8) The method for measuring 1,5-anhydroglucitol according to any one of the above (1) to (7), wherein the 1,5-anhydroglucitol is electrochemically measured in the presence of a stabilizer.

(9) The method for measuring 1,5-anhydroglucitol according to the above (8), wherein the stabilizer is 2-sulfobenzoic acid or 3-sulfobenzoic acid.

(10) The method for measuring 1,5-anhydroglucitol according to any one of the above (1) to (9), wherein the 1,5-anhydroglucitol is electrochemically measured by amperometry, coulometry, or cyclic voltammentry.

(11) The method for measuring 1,5-anhydroglucitol according to any one of the above (1) to (10), wherein the 1,5-anhydroglucitol is electrochemically measured using an electrode having a working electrode for measuring 1,5-anhydroglucitol that contains an oxidoreductase for measuring 1,5-anhydroglucitol and a redox mediator, and a counter electrode.

(12) The method for measuring 1,5-anhydroglucitol according to the above (11), wherein the 1,5-anhydroglucitol is electrochemically measured using a differential electrode.

(13) The method for measuring 1,5-anhydroglucitol according to the above (12), wherein the differential electrode is an electrode having a working electrode for measuring 1,5-anhydroglucitol which contains an oxidoreductase for measuring 1,5-anhydroglucitol and a redox mediator, a working electrode for measuring a blank which contains a redox mediator but does not contain an oxidoreductase for measuring 1,5-anhydroglucitol, and a counter electrode.

(14) A sensor chip for measuring 1,5-anhydroglucitol in whole blood, comprising an electrode having a working electrode for measuring 1,5-anhydroglucitol that contains an oxidoreductase for measuring 1,5-anhydroglucitol and a redox mediator and a counter electrode.

(15) The sensor chip for measuring 1,5-anhydroglucitol in whole blood according to the above (14), further comprising a reagent for eliminating or converting glucose and/or a derivative thereof.

(16) The sensor chip for measuring 1,5-anhydroglucitol in whole blood according to the above (14) or (15), comprising a differential electrode comprising an electrode having a working electrode for measuring 1,5-anhydroglucitol that contains an oxidoreductase for measuring 1,5-anhydroglucitol and a redox mediator, a working electrode for measuring a blank that contains a redox mediator but does not contain an oxidoreductase for measuring 1,5-anhydroglucitol, and a counter electrode.

(17) A kit for measuring 1,5-anhydroglucitol in whole blood, comprising the sensor chip according to any one of the above (14) to (16), a lancet device used for collection of blood, and a measurement device for 1,5-anhydroglucitol.

(18) The kit for measuring 1,5-anhydroglucitol in whole blood according to the above (17), further comprising a reagent for eliminating or converting glucose and/or a derivative thereof.

Advantageous Effect of the Invention

According to the present invention, since 1,5-anhydroglucitol can be electrochemically measured using whole blood as a specimen, and blood cells do not need to be separated, measurement becomes simple without requiring use of a centrifuge or the like, enabling measurement by patients themselves at home.

BEST MODE FOR CARRYING OUT THE INVENTION

Hereafter, the present invention will be explained in detail.

The present invention is a method for electrochemically measuring 1,5-anhydroglucitol in blood that is subject to interference of glucose, characterized in that whole blood is used as a specimen without requiring separation of blood cells in measurement of 1,5-anhydroglucitol in blood. Specifically, the method for measuring 1,5-anhydroglucitol of the present invention is characterized in that glucose and/or a derivative thereof is eliminated or converted from whole blood as it is without separating blood cells, and further an enzyme for measuring 1,5-anhydroglucitol is allowed to act without separating blood cells to electrochemically measure 1,5-anhydroglucitol. Since an enzyme for measuring 1,5-anhydroglucitol also acts on glucose as a substrate as described above, glucose and/or a derivative thereof needs to be eliminated or converted to prevent interference of glucose.

The step of eliminating or converting glucose and/or a derivative thereof and the step of measuring 1,5-anhydroglucitol in the measuring method of the present invention may be performed successively or sequentially with another step therebetween.

Whole blood used in the present invention is blood in a state as collected of which blood cells are not separated, and may contain an anti-coagulant, a glycolytic inhibitor, and/or the like contained in a blood-collecting vessel for blood collection, such as heparin, sodium fluoride, and monoiodoacetic acid. When stored blood is used, blood is preferably collected by a blood-collecting vessel containing sodium fluoride and heparin. Furthermore, the whole blood of the present invention also includes blood collected with a lancet device or the like used for self-measurement of blood sugar levels without a blood-collecting vessel or the like. Blood collection sites are not particularly limited, and include a tip of a finger as well as the outside of the forearm, the abdominal wall, or the outside of the upper arm. The amount of blood collected is, for example, 50 μL or less, preferably, 0.1 to 30 μL. More preferably, 3 to 20 μL is sufficient.

The step of eliminating or converting glucose and/or a derivative thereof to a substance that does not interfere with the measurement in the present invention is not particularly limited so long as it does not affect measurement of target 1,5-anhydroglucitol in blood. Examples thereof include the methods of eliminating or converting glucose and/or a derivative thereof to a substance that does not interfere with measurement described in PATENT DOCUMENTS 1 to 9. The methods using enzymes are more preferred, and examples thereof include methods of enzymatically oxidizing or enzymatically phosphorylating glucose.

Elimination or conversion of glucose in whole blood with enzymes has progressed without any problem contrary to the above-mentioned expectation, and this has enabled measurement of 1,5-anhydroglucitol in whole blood as shown in the examples described later.

Examples of the method for enzymatically oxidizing glucose include a method comprising oxidizing glucose with glucose oxidase, a method comprising oxidizing glucose with glucose dehydrogenase in the presence of a coenzyme nicotinamide adenine dinucleotide (NAD) or nicotinamide adenine dinucleotide phosphoric acid (NADP). Examples of the method for enzymatically phosphorylating glucose include a method comprising phosphorylating glucose with hexokinase or glucokinase to convert to glucose-6-phosphate. Depending on the types of enzymes used for measurement of 1,5-anhydroglucitol, glucose-6-phosphate produced by phosphorylation of glucose may need to be further converted. In this case, examples thereof include a method comprising oxidizing glucose to gluconolactone-6-phosphate with glucose-6-phosphate dehydrogenase in the presence of a coenzyme $NAD^+$ or $NADP^+$, a method comprising allowing hexokinase, phosphohexose isomerase, and 6-phosphofructokinase to act in the presence of adenosine-5'-diphosphate (ADP) and adenosine-5'-triphosphate (ATP) to convert glucose to fructose-1,6-diphosphate, and a method comprising allowing glucose isomerase, fructokinase, and 6-phosphofructokinase to act in the presence of nucleoside diphosphate (NDP) and nucleoside triphosphate (NTP) to convert glucose to fructose-1,6-diphosphate.

Above all, the method of phosphorylating glucose with hexokinase or glucokinase is more preferred. For example, a method of phosphorylating glucose by enzymatic cycling method with hexokinase or glucokinase in the presence of magnesium ion, ATP, phosphoenolpyruvate (PEP) and pyruvate kinase (PK) is particularly preferred.

Enzymes used for the above-mentioned conversions are not particularly limited so long as they do not require 1,5-anhydroglucitol as a substrate, and examples thereof include enzymes classified as glucose oxidase (EC1.1.3.4), glucose dehydrogenases (EC1.1.1.47, EC1.1.1.118, EC1.1.1.119, and EC1.1.99.10), hexokinase (EC2.7.1.1), glucokinase (EC2.7.1.2), glucose-6-phosphate ketol isomerase (EC5.3.1.9) as phosphohexose isomerase, glucose isomerase (EC5.3.1.18), fructokinase (EC2.7.1.4), and phosphohexokinase (EC2.7.1.11) as 6-phosphofructokinase according to the IUPAC-IUB nomenclature. Those commercially available can also be used. There is no problem for using as a hexokinase is an NDP-dependent hexokinase, such as ADP-dependent hexokinase in particular.

Furthermore, in the method comprising oxidizing glucose with glucose oxidase and glucose dehydrogenase, gluconolactonase (EC3.1.1.17) can also be used to convert the generated glucono-1,5-lactone completely to gluconic acid, and mutarotase (EC5.1.3.3) may be used in combination, if necessary.

In the measurement method of the present invention, hexokinase or glucokinase that phosphorylates both glucose and 1,5-anhydroglucitol can also be used in the method comprising converting 1,5-anhydroglucitol to 1,5-anhydroglucitol-6-phosphate and measuring using an enzyme that acts on 1,5-anhydroglucitol-6-phosphate.

Conversion of glucose and/or a derivative thereof to a substance that does not interfere with measurement in the present invention is performed by, for example, bringing a converting reagent and whole blood into contact with each other. Specifically, these substances may be mixed in a container beforehand, or the converting reagent may be carried on a sensor chip described later. Examples of the converting reagent include a solution consisting of hexokinase (HK) and/or glucokinase (GK), pyruvate kinase (PK), adenosine-5'-triphosphate (ATP), phosphoenolpyruvate (PEP), magnesium chloride or magnesium sulfate, and potassium chloride, and a dried agent of the solution.

Hexokinase is preferably derived from yeasts, and glucokinase is preferably derived from *Bacillus stearothermophilus*. The converting reagent may contain both hexokinase and glucokinase or either one of them. The concentration of hexokinase and/or glucokinase in the converting reagent solution is 1 to 500 U/mL, preferably 20 to 300 U/mL.

The concentration of pyruvate kinase in the converting reagent solution is 1 to 500 U/mL, preferably 20 to 300 U/mL. The concentration of ATP is 1 to 200 mM, preferably 10 to 80 mM. The concentration of phosphoenolpyruvate is 10 to 1500 mM, preferably 100 to 500 mM. The concentration of magnesium chloride or magnesium sulfate is 1 to 200 mM, preferably 5 to 50 mM. The concentration of potassium chloride is 1 to 200 mM, preferably 5 to 50 mM.

Furthermore, the addition of an enzyme that acts on each interfering substance, such as an ascorbic acid oxidase, a uric acid oxidase, or a bilirubin oxidase, to a converting reagent is effective to prevent interference of measurement by interfering substances other than glucose. For example, the concentration of an ascorbate oxidase in the converting reagent solution is 1 to 1000 U/mL, preferably 5 to 500 U/mL.

The step of electrochemically measuring 1,5-anhydroglucitol in whole blood using enzymes will be explained below. Examples of methods for the measurement include a method comprising directly measuring hydrogen peroxide generated by an oxidation reduction reaction with an enzyme and a method using a redox mediator that mediates electron transfer involved in an oxidation reduction reaction.

Examples of the enzymes include enzymes oxidizing 1,5-anhydroglucitol, and oxidoreductases are more preferred. Examples thereof include enzymes classified as pyranose oxidase (EC1.1.3.10), L-sorbose oxidase (EC1.1.3.11), L-sorbose dehydrogenase (EC1.1.99.12), 1,5-anhydroglucitol dehydrogenase (EC1.1.99.13) according to the IUPAC-IUB nomenclature.

Examples of the oxidoreductases include pyranose oxidase produced by Basidiomycetous fungi No. 52 (International Patent Organism Depositary, National Institute of Advanced Industrial Science and Technology: Accession No. FERM P-10106) described in PATENT DOCUMENT 12, *Polyporus obtusus* ATCC26733 described in PATENT DOCUMENT 7, and the like, L-sorbose oxidases produced by *Trametes sanguinea* IF04923, L-sorbose dehydrogenase produced by *Gluconobacter oxydans* UV-10 (International Patent Organism Depositary, National Institute of Advanced Industrial Science and Technology: Accession No. FERM P-8422) described in PATENT DOCUMENT 13 and the like, 1,5-anhydroglucitol dehydrogenase produced by *Pseudomonas* sp. NK-85001 (International Patent Organism Depositary, National Institute of Advanced Industrial Science and Technology: Accession No. FERM BP-1037) described in PATENT DOCUMENT 11 and the like, 1,5-anhydroglucitol dehydrogenase produced by fungi such as *Eupenicillium crustaceum* IFO-8938 described in PATENT DOCUMENT 14 and the like; 1,5-anhydroglucitol dehydrogenase produced by *Trichoderma longibrachiatum* KDK3003 (International Patent Organism Depositary, National Institute of Advanced Industrial Science and Technology: Accession No. FERM BP-6458) described in PATENT DOCUMENT 15 and the like, 1,5-anhydroglucitol dehydrogenase produced by *Rahnella aquatilis* 474 (International Patent Organism Depositary, National Institute of Advanced Industrial Science and Technology Accession No. FERM P-16158), *Enterobacter cloacae* 340 (International Patent Organism Depositary, National Institute of Advanced Industrial Science and Technology Accession No. FERM P-16157) and *Serratia marcescens* 825 (International Patent Organism Depositary, National Institute of Advanced Industrial Science and Technology Accession No. FERM P-16159) described in PATENT DOCUMENT 16 and the like, 1,5-anhydroglucitol dehydrogenase produced by *Agrobacterium tumefaciens* NT1130 strain (International Patent Organism Depositary, National Institute of Advanced Industrial Science and Technology: Accession No. FERM BP-5997) described in PATENT DOCUMENT 6, which can dehydrogenate 1,5-anhydroglucitol without requiring an electron acceptor, D-glucoside-3-dehydrogenase produced by *Cytophaga marinoflava* ATCC19326 described in PATENT DOCUMENT 10 and the like, and enzymes described PATENT DOCUMENTS 17, 18, and 12. Furthermore, other commercially available oxidoreductases that oxidize 1,5-anhydroglucitol can also be used.

Of these, pyranose oxidase, L-sorbose oxidase, and 1,5-anhydroglucitol dehydrogenase are more preferred.

Furthermore, after identifying and improving or modifying the genes of these enzymes by usual gene manipulation techniques, then enzymes produced using recombinant *Escherichia coli* or the like can also be used in the measurement method of the present invention so long as they are oxidoreductases requiring 1,5-anhydroglucitol as a substrate.

Examples of electrochemical measurement methods include amperometry (method comprising measuring an electric current), coulometry (method comprising measuring an amount of electricity), a potential sweep method, and cyclic voltammetry. Of these, amperometry and coulometry are more preferred.

An electrode used in electrochemical measurement methods can be formed on an insulating board, using gold, platinum, carbon, palladium, silver, or silver-silver chloride. Examples of materials of the insulating board include plastic such as polyethylene terephthalate, polycarbonate, and polyvinyl carbonate and glass, and polyethylene terephthalate is more preferred. An electrode can be formed on this board by screen printing, vacuum deposition, sputtering, or the like. Of these methods, screen printing is more preferred. Specifically, it is preferable to form an electrode by screen-printing a conductive carbon ink or silver-silver chloride on a board made of polyethylene terephthalate using and quenching the board at 100 to 150° C.

As an electrode used in the electrochemical measurement of 1,5-anhydroglucitol of the present invention, either a three-electrode forming a working electrode, a counter electrode, and a reference electrode or a two-electrode forming a working electrode and a counter electrode can be used. In general, in measurement using a three-electrode, a potential is applied to a working electrode using a reference electrode as a reference, and an electric current that flows between the working electrode and a counter electrode is measured. In measurement using a two-electrode, a counter electrode is used as a reference electrode, a predetermined potential is applied to a working electrode using the counter electrode as reference, and an electric current that flows between the working electrode and the counter electrode is measured.

Various methods are available for electrochemical measurement, and examples in the present invention include measurement methods comprising measuring generated hydrogen peroxide directly using a hydrogen peroxide electrode and measurement method using a redox mediator that mediates electron transfer involved in an oxidation reduction reaction.

Examples of the redox mediator include oxidation mediators and reduction mediators, and oxidation mediators are more preferred. Of these, osmium complexes, quinone compounds, ferrocene compounds, phenothiazine compounds, phenoxazine compounds, phenazine compounds, indophenol compounds, diphenylamine compounds, phenol compounds, and the like are more preferred. Examples of osmium complexes include $[Os(III)(bipyridyl)_2(imidazoyl)Cl]Cl_2$ and polymers thereof. Examples of quinone compounds include benzoquinone, 2-methylbenzoquinone, 2,6-dimethylbenzoquinone, 2,6-dichlorobenzoquinone, 2,5-dihydroxybenzoquinone, 2-hydroxy-1,4-naphthoquinone, 2-methyl-1,4-naphthoquinone, 2,3-dimethoxy-5-methyl-1,4-benzoquinone, pyrroloquinoline quinone (PQQ), and ubiquinone. Examples of ferrocene compounds include ferrocenyl PEG, ferrocenyl TMA, N,N-dimethylaminomethyl ferrocene, and ferrocene methanol. Examples of phenothiazine compounds include thionine, methylene blue, methylene green, 10-(carboxymethylaminocarbonyl)-3,7'-bis(dimethylamino)-phenothiazine sodium salts, toluidine blue O, azure I, azure C, azure A, new methylene blue, and benzoyl leukomethylene blue. Examples of phenoxazine compounds include meldola blue. Examples of phenazine compounds include phenazine methosulfate, 1-methoxyphenazine methosulfate, safranine, and phenosafranine. Examples of indophenol compounds include 2-dichlorophenol-indophenol (DCIP). Examples of diphenyl amine compounds include 4,4'-bis(dimethylamino)diphenylamine, N-(carboxymethylaminocarbonyl)-4,4'-bis(dimethylamino)diphenylamine sodium salt, N-methyl-N-phenyl-1,4-phenylenediamine hydrochloride, and N-methyl-N-(3-methoxyphenyl)-1,4-phenylenediamine hydrochloride. Examples of phenol compounds include p-aminophenol.

In addition, examples of mediators that can be used in the present invention include ferricyanine compounds (potassium ferricyanide etc.), ruthenium complexes or polymers thereof, bipyridine compounds (methyl viologen etc.), triphenyl methane compounds (malachite green, TPM-PS etc.), benzothiazoline compounds (2-hydrazono-2,3-dihydro-3-methyl-6-benzothiazole, sulfonates thereof, etc.), cyanine compounds (gallocyanine, phthalocyanine, phycocyanine etc.), azo compounds (Magenta J-3GL, Yellow C-Y9, Black C-BK4 etc.), bipyridylazo compounds (5-Br-PSAA, 5-Br-PAPS, TAMSMB, etc.), aniline and derivatives thereof (DAPS, HALPS, ADPS, ALPS, TOOS, ALOS etc.), polyaniline and derivatives thereof, phenol compounds (p-aminophenol etc.), phenylene diamine compounds (Baliamine blue B, 2,3,5,6-tetramethyl-p-phenylene diamine etc.), Rhodamine compounds (Rhodamine B etc.), xanthene compounds (pyronin Y, pyronin B, fluorescein sodium etc.), isoalloxazine compounds (riboflavin, FAD etc.), indigo compounds (indigo trisulfonic acid, indigo carmine etc.), phenanthroline compounds (bathocuproin sulfonate sodium, bathophenanthroline sulfonate sodium etc.), sulfophthalein compounds (methylthymol blue etc.), benzidine compounds (TMBZ, TMBZ·PS, DAB, anisidine blue etc.), tetrazolium compounds (WST-1, MTT, Nitro-TB, XTT etc.), cytochrome C, lumichrome, ferredoxins, EDTAs, NAD, and NADP.

The compounds such as the above-mentioned enzymes and redox mediators carried by the electrode in the electrochemical measurement of 1,5-anhydroglucitol of the present invention are dissolved in purified water or a suitable buffer solution as an electrode reagent and applied on an electrode as an electrode reagent solution.

The concentration of the above-mentioned redox mediator contained in the electrode reagent is, for example, approx. 0.01 μM to 1 M, preferably 0.1 μM to 200 mM as the concentration in the electrode reagent solution obtained by dissolution in purified water or a suitable buffer solution to be applied on an electrode. The concentration of the above-mentioned enzyme is, for example, approx. 0.1 to 5000 U/mL, preferably 1 to 2000 U/mL as the concentration in the electrode reagent solution obtained by dissolution in purified water or a suitable buffer solution to be applied on an electrode. As the buffer solution, buffers used in usual biochemical reactions can be used, and examples thereof include 2-morpholinoethanesulfonic acid (MES) buffer, 2-[4-(2-hydroxyethyl)-1-piperazinyl]ethanesulfonic acid (HEPES) buffer, N-tris(hydroxymethyl)methyl-3-aminopropanesulfonic acid (TAPS) buffer, tris buffer, and phosphate buffer. The pH is 3 to 10, preferably 5 to 9. The buffer solution concentration is 1 mM to 1 M, preferably 5 to 500 mM.

The electrode reagent solution preferably contains low molecular weight compounds such as sulfobenzoic acid, sugar, and sugar alcohol, proteins such as albumin, or hydrophilic macromolecular compounds such as carboxymethylcellulose, polyethylene glycol, polyvinyl alcohol, and polyvinylpyrrolidone as stabilizers that increase stability of enzymes and redox mediators, resulting in stable measurement of 1,5-anhydroglucitol over a long period and measurement of 1,5-anhydroglucitol in blood with favorable precision. Preferred examples of sulfobenzoic acid include 2-sulfobenzoic acid and 3-sulfobenzoic acid. When a low molecular weight compound such as sulfobenzoic acid is used as the stabilizer, the concentration thereof is approx. 0.1 to 500 mM, preferably approx. 1 to 100 mM as the concentration in the electrode reagent solution to be applied on the electrode. When a hydrophilic macromolecular compounds such as albumin is used as the stabilizer, the concentration thereof is, for example, approx. 0.01 to 20%, preferably approx. 0.02 to 10% as the concentration in the electrode reagent solution to be applied on the electrode.

The above-mentioned electrode is preferably allowed to carry the above-mentioned electrode reagent. This can be achieved by a known method. For example, a predetermined amount of the above-mentioned electrode reagent is applied on an electrode by spotting, dipping, or spin coating, and dried. Furthermore, in addition to such physical adsorption, the above-mentioned electrode reagent may be chemically bound to an electrode.

To be carried on an electrode, the above-mentioned stabilizer is added to the above-mentioned electrode reagent solution and then applied and dried or laminated on a layer in which an enzyme or the like is carried.

The differential electrode will be explained below.

A differential electrode is, for example, an electrode which has a working electrode that carries an oxidation reduction enzyme and a redox mediator reagent (e.g., a working electrode for measuring 1,5-anhydroglucitol), a working electrode that carries a redox mediator reagent but does not contain an oxidation reduction enzyme (e.g., a working electrode for measuring a blank), and a counter electrode, simultaneously measures a specimen containing an interfering substance related to the redox mediator or the like using the working electrode that carries an oxidation reduction enzyme and a redox mediator reagent and the working electrode that carries a redox mediator reagent but does not contain an oxidation reduction enzyme, and removes the effect of the interfering substance by deducting a signal part by the interference, and the structure thereof is not limited so long as it performs such an action. Examples thereof include differential electrodes having a working electrode for measuring 1,5-anhydroglucitol that contains an oxidoreductase and a redox mediator for measuring 1,5-anhydroglucitol, a working electrode for measuring a blank that contains a redox mediator, and a counter electrode in the examples described later.

This electrochemical measurement method using a differential electrode is referred to as a differential method, and measurement of glucose as a target is known. In this case, the interfering substances are uric acid and ascorbic acid. The blood concentration of uric acid is 120 to 770 μmol/L and that of ascorbic acid is 11 to 210 μmol/L based on 5500 to 33,000 μmol/L of glucose. These concentrations are much lower than that of glucose.

Meanwhile, the concentration of 1,5-anhydroglucitol in blood is 6 to 300 µmol/L, which is much lower than that of glucose. In electrochemical measurement of 1,5-anhydroglucitol in blood, uric acid and ascorbic acid are similarly interfering substances. However, the concentration of these substances are almost equal to or more than that of 1,5-anhydroglucitol.

That is, differential methods employed when the concentration of an interfering substance is significantly lower than that of a substance to be measured are known, but no differential method employed when the concentration of an interfering substance is equal to or higher than that of a substance to be measured has been reported so far. Therefore, whether the differential method is effective, and correct measurement results can be obtained even when an interfering substance (uric acid, ascorbic acid) having a concentration equal to or more than that of 1,5-anhydroglucitol (substance to be measured) exists is not known.

The sensor chip for measuring 1,5-anhydroglucitol of the present invention is composed of the above-mentioned electrode formed on an insulating board, a junction part to be connected to a measurement device, a lead part that connects the electrode and the junction part, further a resist (insulating part) for making the area of the electrode constant to insulate the lead part, and the like, further including a port for collecting blood as a specimen, a space into which blood enters, a fluid channel, and the like. This structure is formed with a film material such as a polyethylene film or a polyimide film, an adhesive such as a hot-melt adhesive, a taping agent such as a double-sided adhesive tape, and the like.

1,5-anhydroglucitol can also be measured using a sensor chip in which an electrode reagent is not carried by an electrode, and a specimen and the reagent are mixed beforehand and added. However, a sensor chip including an electrode having a working electrode for measuring 1,5-anhydroglucitol that contains an oxidoreductase for measuring 1,5-anhydroglucitol and a redox mediator and a counter electrode is preferred, and a sensor chip including a differential electrode having a working electrode for measuring 1,5-anhydroglucitol that contains an oxidoreductase for measuring 1,5-anhydroglucitol and a redox mediator, a working electrode for measuring a blank that contains a redox mediator but does not contain an oxidoreductase, and a counter electrode is more preferred. The counter electrode may carry the above-mentioned electrode reagent, if necessary.

Furthermore, a sensor chip having a pretreatment part containing a reagent performing the step of converting glucose and/or a derivative thereof to a substance that does not interfere with the measurement may be used.

Simplified diagrams of one example of the sensor chip used in the present invention are shown in FIGS. 1 to 3.

The present invention also includes a kit for measuring 1,5-anhydroglucitol in whole blood composed of at least the above-mentioned sensor chip, a lancet device used for blood collection, and a measurement device for 1,5-anhydroglucitol. The lancet device may be similar to a lancet device attached to a device for self-monitoring of blood sugar levels. This kit may further include a reagent used in the step of converting glucose and/or a derivative thereof to a substance that does not interfere with the measurement.

Furthermore, this kit for measuring 1,5-anhydroglucitol may have a device for collecting a sample, a reagent for pretreatment, a calibrator, and the like. The device for collecting a sample is not particularly limited so long as about several tens µL or less of whole blood can be collected, and may be similar to a capillary used in measurement of hematocrit.

Hereafter, the present invention will be explained more specifically with reference to the following examples and reference examples. However, these examples only show one aspect of the present invention and do not limit the scope of the present invention. The enzymes that were obtained by known methods or were commercially available were used in the examples.

The electrochemical detector used in all the examples and Reference Examples 9, 10, and 11 was 8-CH Multipotentiostat MODEL PS-08 equipped with GPIB RS232C manufactured by Toho Giken, and the electrochemical detector used in Reference Examples 7 and 8 was 8-CH Multipotentiostat MODEL PS-08 equipped with a function generator FG-02 manufactured by Toho Giken.

1,5AG in the figures denotes 1,5-anhydroglucitol.

Example 1

1) Glucose-Converting Reagent

1) Glucose-Converting Reagent

In 10.0 mM MES buffer, 17.6 mM $MgCl_2$, 17.6 mM KCl, 175.7 mM phosphoenolpyruvate (PEP), 17.6 mM ATP, 123 U/mL pyruvate kinase (PK), 75 U/mL glucokinase, 200 U/mL ascorbic acid oxidase, 100 mM sodium chloride, 0.1% $NaN_3$, 0.1 mM EDTA, and 0.06% bovine serum albumin (BSA) were dissolved as the composition after the pH was adjusted to 7.0 using 1 N aqueous sodium hydroxide to prepare a glucose-converting reagent.

2) Electrode Reagent Solution 23.6 mM osmium(III) complex ($[Os(III)(bipyridyl)_2(imidazoyl)Cl]Cl_2$) described in Japanese Patent No. 3713049, 930 U/mL pyranose oxidase (derived from Basidiomycetous fungi No. 52), and 50 mM 3-sulfobenzoic acid were dissolved in purified water in this composition to prepare an electrode reagent solution.

3) Sensor Chip

A carbon ink (product name, Carbon Paste TU15ST: Asahi Chemical Research Laboratory Co., Ltd.) was screen-printed on a base plate made of polyethylene terephthalate at a thickness of 10 µm and quenched at 150° C. for 40 min to form a working electrode and a lead part and a counter electrode and a lead part. Then, a resist ink (product name, CR18G-KF: Asahi Chemical Research Laboratory Co., Ltd.) was screen-printed on a portion except the electrode parts and a junction with a measurement device at a thickness of 20 µm and quenched at 130° C. for 15 minutes. Thus an electrode 11 shown in FIG. 1 was prepared.

The electrode 11 was coated with 4 µL of the electrode reagent solution obtained in the above 2) at a position 1 at which the specimen was applied and dried at 50° C. for 13 minutes to prepare a sensor chip.

4) Creation of Calibration Curve

To create a calibration curve of 1,5-anhydroglucitol, 5 specimens obtained by adding 20 µL each of 1,5-anhydroglucitol preparations at known concentrations (the concentration of 1,5-anhydroglucitol in the specimens obtained by the procedure in Reference Example 1 described later, except the blood cell separation procedure, were 3.8, 7.8, 15.8, 31.4, and 63.9 µg/mL) to plasma and 10 µL of the glucose-converting reagent were mixed in Eppendorf tubes and left stand for 5 minutes. Then, 10 μL each of the reaction mixture was applied dropwise on the electrode 11 at the position 1 at which the specimen was applied. 80 seconds later, 0.15 V was applied to the working electrode with respect to the counter electrode for 10 seconds, and current values after following 5 seconds were measured with an electrochemical detector (8-CH Multipotentiostat MODEL PS-08 equipped with GPIB RS232C: Toho Giken). A calibration curve was created from differences between the coulomb levels obtained from the sensor chip for measuring 1,5-anhydroglucitol and those obtained from the sensor chip for measuring a blank, and the concentrations of 1,5-anhydroglucitol.

5) 1,5-Anhydroglucitol Measurement Procedure

20 μL each of whole blood from 3 normal subjects with uric acid levels almost equal to those of the specimens obtained in the above 4) or with low uric acid levels in the measured specimens was mixed with 10 μL of the glucose-converting reagent in Eppendorf tubes and left stand for 5 minutes. Then, 10 μL each of the reaction mixture was applied dropwise on the electrode 11 at the position 1 at which the specimen was applied. 80 seconds later, 0.15 V was applied to the working electrode with respect to the counter electrode for 10 seconds, and current values after following 5 seconds were measured with an electrochemical detector. The amounts of 1,5-anhydroglucitol in whole blood of 3 specimens were obtained using the calibration curve created in the above 4). The results are shown in Table 1. The mean values of 4 measurements were used for the specimens for creation of the calibration curve, and the value of 1 measurement was used for the specimens.

Reference Example 1

The same whole blood specimens from the 3 normal subjects used for the measurement in 5) of Example 1 were centrifuged at 3000 rpm for 10 minutes, and the supernatants (plasma) was measured for 1,5-anhydroglucitol using a 1,5-anhydroglucitol measurement reagent (Lana 1,5AG Auto Liquid: Nippon Kayaku Co., Ltd.) and Automated Analyzer 7150 (Hitachi, Ltd.) with the following parameters. The results are shown in Table 1.

| Analytical method | 2 points |
| Reading point | 24-50 |
| Volume of specimen | 8 μL |
| Lana 1,5AG Auto Liquid Pretreatment reagent (R1) | 240 μL |
| Lana 1,5AG Auto Liquid Color reagent (R2) | 120 μL |
| Temperature | 37° C. |
| Measurement wavelength (sub/main) | 700/546 nm |

TABLE 1

|  | 1,5-Anhydroglucitol concentration (μg/mL) | |
| --- | --- | --- |
|  | Reference Example 1 | Example 1 |
| Whole blood specimen 1 | 9.8 | 10.4 |
| Whole blood specimen 2 | 15.6 | 16.8 |
| Whole blood specimen 3 | 17.2 | 17.2 |

When the glucose-converting reagent was allowed to act on whole blood to convert glucose to a substance that does not interfere with measurement and react with an electrode reagent without separating blood cells, the measured values of 1,5-anhydroglucitol in whole blood specimens (Example 1) were consistent well with those obtained by a known measurement method in Reference Example 1 (correlation coefficient, 0.9881), suggesting that 1,5-anhydroglucitol in whole blood can be measured by the present invention.

Example 2

1) Glucose-Converting Reagent

In 10.0 mM MES buffer, 17.6 mM $MgCl_2$, 17.6 mM KCl, 175.7 mM phosphoenolpyruvate (PEP), 17.6 mM ATP, 123 U/mL pyruvate kinase (PK), 97 U/mL hexokinase, and 20 U/mL ascorbic acid oxidase were dissolved as the composition after the pH was adjusted to 3.0 using 1 N aqueous sodium hydroxide to prepare a glucose-converting reagent.

2) Electrode Reagent Solution (i) For measuring 1,5-anhydroglucitol
23.6 mM osmium(III) complex ($[Os(III)(bipyridyl)_2(imidazoyl)Cl]Cl_2$) and 465.2 U/mL pyranose oxidase (derived from Basidiomycetous fungi No. 52) were dissolved in purified water in this composition to prepare an electrode reagent solution.
(ii) For Measuring Blank
23.6 mM osmium(III) complex ($[Os(III)(bipyridyl)_2(imidazoyl)Cl]Cl_2$) was dissolved in purified water in this composition to prepare an electrode reagent solution.

3) Sensor Chip

Two electrodes 11 prepared by the same manner as in 3) of Example 1 were prepared, and 4 μL of each of the electrode reagent solutions for measuring 1,5-anhydroglucitol or a blank in the above 2) was applied on each of the electrodes at the position 1 at which the specimen was applied and dried at 50° C. for 13 minutes to prepare sensor chips for measuring 1,5-anhydroglucitol and a blank.

4) Creation of Calibration Curve

To create a calibration curve of 1,5-anhydroglucitol, 20 μL each of 5 specimens obtained by adding 1,5-anhydroglucitol preparations with known concentrations (the concentrations of 1,5-anhydroglucitol in the specimens obtained by the procedure in Reference Example 1 except the blood cell separation procedure were 9.4, 18.8, 37.5, 75.0, and 150.0 μg/mL) to plasma was mixed with 10 μL of the glucose-converting reagent in Eppendorf tubes and left stand for 5 minutes. Then, 10 μL each of the reaction mixtures was applied dropwise on each of the electrodes 11 for measuring 1,5-anhydroglucitol and a blank at the position 1 at which the specimen was applied. 80 seconds later, 0.15 V was applied to the working electrode with respect to the counter electrode for 10 seconds, and current values after following 5 seconds were measured with an electrochemical detector. A calibration curve was created from the differences between the current values obtained from the sensor chip for measuring 1,5-anhydroglucitol and those obtained from the sensor chip for measuring a blank and concentrations of 1,5-anhydroglucitol.

5) Measurement of 1,5-Anhydroglucitol

20 μL each of whole blood from 6 normal subjects for measuring 1,5-anhydroglucitol was mixed with 10 μL of a glucose-converting reagent in Eppendorf tubes and left stand for 5 minutes. Then, 10 µL of each reaction mixture was applied dropwise on each of the electrodes 11 for measuring 1,5-anhydroglucitol and a blank at the position 1 at which the specimen was applied. 80 seconds later, 0.15 V was applied to the working electrode with respect to the counter electrode for 10 seconds, and current values after following 5 seconds were measured with an electrochemical detector. The differences between the current values obtained from the sensor chip for measuring 1,5-anhydroglucitol and the current values obtained from the sensor chip for measuring a blank were compared with the calibration curve to obtain the amounts of 1,5-anhydroglucitol in whole blood of the 6 specimens. The results are shown in Table 2. The mean values of 4 measurements were used for the specimens for creation of the calibration curve, and the value of 1 measurement was used for the specimens.

Reference Example 2

The same whole blood specimens as measured in 5) of Example 2 was measured for 1,5-anhydroglucitol by the same manner as in Reference Example 1. The results are shown in Table 2.

TABLE 2

|  | 1,5-Anhydroglucitol concentration (µg/mL) | |
| --- | --- | --- |
|  | Reference Example 2 | Example 2 |
| Whole blood specimen 4 | 16.4 | 16.7 |
| Whole blood specimen 5 | 17.5 | 14.2 |
| Whole blood specimen 6 | 26.2 | 23.5 |
| Whole blood specimen 7 | 31.5 | 26.9 |
| Whole blood specimen 8 | 27.2 | 24.4 |
| Whole blood specimen 9 | 31.4 | 36.7 |

When the glucose-converting reagent was allowed to act on whole blood to convert glucose to a substance that does not interfere with measurement, and whole blood was reacted with the electrode reagent without separating blood cells, the measured values of 1,5-anhydroglucitol in whole blood obtained by the differential method were correlated well with those obtained by measurement in Reference Example 2 (correlation coefficient, 0.8943), suggesting that 1,5-anhydroglucitol in whole blood can be measured by the present invention.

Example 3

1) Glucose-Converting Reagent

The glucose-converting reagent obtained in 1) of Example 1 was used.

2) Electrode Reagent Solution (i) For measuring 1,5-Anhydroglucitol
23.6 mM osmium(III) complex ($[Os(III)(bipyridyl)_2(imidazoyl)Cl]Cl_2$), 930 U/mL pyranose oxidase (derived from Basidiomycetous fungi No. 52), and 50 mM 3-sulfobenzoic acid were dissolved in purified water in this composition to prepare an electrode reagent solution.

(ii) For Measuring Blank
23.6 mM osmium(III) complex ($[Os(III)(bipyridyl)_2(imidazoyl)Cl]Cl_2$) and 50 mM 3-sulfobenzoic acid were dissolved in purified water in this composition to prepare an electrode reagent solution.

3) Sensor Chip

A sensor chip for measuring 1,5-anhydroglucitol and a sensor chip for measuring a blank were prepared by the same manner as in the above 3) of Example 2.

4) Creation of Calibration Curve

To create a calibration curve of 1,5-anhydroglucitol, 20 µL each of 5 specimens obtained by adding 1,5-anhydroglucitol preparations with known concentrations (the concentrations of 1,5-anhydroglucitol of the specimens obtained by the procedure in Reference Example 1 except the blood cell separation procedure were 9.5, 19.6, 39.6, 78.5, and 159.8 µg/mL) to plasma was mixed with 10 µL of the glucose-converting reagent in Eppendorf tubes and left stand for 5 minutes. Then, 10 µL each of the reaction mixture was applied dropwise on each of the electrodes 11 for measuring 1,5-anhydroglucitol and for measuring a blank at the position 1 at which the specimen was applied. 80 seconds later, 0.15 V was applied to the working electrode with respect to the counter electrode for 10 seconds, and current values after following 5 seconds were measured with an electrochemical detector. A calibration curve was created from the differences between the current values obtained from the sensor chip for measuring 1,5-anhydroglucitol and those obtained from the sensor chip for measuring a blank and concentrations of 1,5-anhydroglucitol.

5) Measurement of 1,5-Anhydroglucitol

20 µL each of whole blood from 6 normal subjects for measuring 1,5-anhydroglucitol was mixed with 10 µL of a glucose-converting reagent in Eppendorf tubes, and the mixture was allowed to stand for 5 minutes. Then, 10 µL of each reaction mixture was applied dropwise at the position 1 at which the specimen was applied of the electrodes 11 for measuring 1,5-anhydroglucitol and for measuring a blank. 80 seconds later, 0.15 V was applied to the working electrode with respect to the counter electrode for 10 seconds, and current values after following 5 seconds were measured with an electrochemical detector. The differences between the current values obtained from the sensor chip for measuring 1,5-anhydroglucitol and the current values obtained from the sensor chip for measuring a blank were compared with the calibration curve to obtain the amounts of 1,5-anhydroglucitol in the 6 whole blood specimens. The results are shown in Table 3. The mean values of 4 measurements were used for the specimens for creation of the calibration curve, and the value of 1 measurement was used for the specimens.

Reference Example 3

The same whole blood specimens as measured in 5) of Example 3 were measured for 1,5-anhydroglucitol by the same manner as in Reference Example 1. The results are shown in Table 3.

TABLE 3

| | 1,5-Anhydroglucitol concentration (µg/mL) | |
|---|---|---|
| | Reference Example 3 | Example 3 |
| Whole blood specimen 10 | 9.8 | 9.7 |
| Whole blood specimen 11 | 15.6 | 15.5 |
| Whole blood specimen 12 | 17.2 | 17.3 |
| Whole blood specimen 13 | 24.6 | 25.1 |
| Whole blood specimen 14 | 30.1 | 32.8 |
| Whole blood specimen 15 | 29.0 | 30.8 |

When the glucose-converting reagent was allowed to act on whole blood to convert glucose to a substance that does not interfere with measurement, and whole blood was reacted with the electrode reagent without separating blood cells, the values of 1,5-anhydroglucitol in whole blood measured by the differential method (Example 3) were correlated well with those measured by a known measurement method in Reference Example 3 (correlation coefficient, 0.9982), suggesting that 1,5-anhydroglucitol in whole blood can be measured by the present invention. Furthermore, the results clearly showed a better correlation than that in the above Example 2 (correlation coefficient, 0.8943). That is, it has been demonstrated that 1,5-anhydroglucitol in whole blood is measured with superior precision by using a stabilizer and a differential method in combination.

Example 4

1) Glucose-Converting Reagent

The glucose-converting reagent of 1) in Example 1 was used.

2) Electrode Reagent Solution (i) For measuring 1,5-Anhydroglucitol
11.8 mM osmium(III) complex ([Os(III)(bipyridyl)$_2$(imidazoyl)Cl]Cl$_2$) and 111.0 U/mL 1,5-anhydroglucitol dehydrogenase (derived from *Pseudomonas* sp. NK-85001) were dissolved in purified water in this composition to prepare an electrode reagent solution.
(ii) For Measuring Blank
To prepare an electrode reagent solution, the component was dissolved in purified water so that the composition should be 11.8 mM osmium(III) complex ([Os(III)(bipyridyl)$_2$(imidazoyl)Cl]Cl$_2$).

3) Sensor Chips

Two of the electrodes 11 prepared by the same manner as in 3) of Example 1 were prepared, 4 µL each of the electrode reagent solutions for measuring 1,5-anhydroglucitol and for measuring a blank obtained in the above 2) was applied on each of the electrodes at the position 1 at which the specimen was applied and dried at 50° C. for 8 minutes to prepare sensor chips for measuring 1,5-anhydroglucitol and for measuring a blank.

4) Creation of Calibration Curve

To create a calibration curve of 1,5-anhydroglucitol, 20 µL each of 3 specimens obtained by adding 1,5-anhydroglucitol preparations with known concentrations (the concentrations of 1,5-anhydroglucitol in the specimens obtained by the procedure in Reference Example 1 except the blood cell separation procedure were 24.2, 49.3, and 98.8 µg/mL) to plasma was mixed with 10 µL of the glucose-converting reagent in Eppendorf tubes and left stand for 5 minutes. Then, 10 µL each of the reaction mixture was applied dropwise on each of the electrodes 11 for measuring 1,5-anhydroglucitol and for measuring a blank at the position 1 at which the specimen was applied. 80 seconds later, 0.15 V was applied to the working electrode with respect to the counter electrode for 10 seconds, and current values after following 5 seconds were measured with an electrochemical detector. A calibration curve was created from the differences between the current values obtained from the sensor chip for measuring 1,5-anhydroglucitol and those obtained from the sensor chip for measuring a blank and the concentrations of 1,5-anhydroglucitol.

5) 1,5-Anhydroglucitol Measurement Procedure

20 µL each of whole blood from 4 normal subjects for measuring 1,5-anhydroglucitol was mixed with 10 µL of the glucose-converting reagent in Eppendorf tubes and left stand for 5 minutes. Then, 10 µL each of the reaction mixture was applied dropwise on each of the electrodes 11 for measuring 1,5-anhydroglucitol and for measuring a blank at the position 1 at which the specimen was applied. 80 seconds later, 0.15 V was applied to the working electrode with respect to the counter electrode for 10 seconds, and current values after following 5 seconds were measured with an electrochemical detector. The differences between the current values obtained from the sensor chip for measuring 1,5-anhydroglucitol and those obtained from the sensor chip for measuring a blank were compared with the calibration curve to obtain the amounts of 1,5-anhydroglucitol in the 4 whole blood specimens. The results are shown in Table 4. The mean values of 4 measurements were used for the specimens for creation of the calibration curve, and the value of 1 measurement was used for the specimens.

Reference Example 4

The same whole blood specimens as measured in Example 4 were measured for 1,5-anhydroglucitol by the procedure in Reference Example 1. The results are shown in Table 4.

TABLE 4

| | 1,5-Anhydroglucitol concentration (µg/mL) | |
|---|---|---|
| | Reference Example 4 | Example 4 |
| Whole blood specimen 16 | 9.4 | 10.0 |
| Whole blood specimen 17 | 14.0 | 13.8 |
| Whole blood specimen 18 | 27.8 | 26.2 |
| Whole blood specimen 19 | 32.7 | 32.6 |

When the glucose-converting reagent was allowed to act on whole blood to convert glucose to a substance that does not interfere with measurement and reacted with the electrode reagent containing 1,5-anhydroglucitol dehydrogenase without separating blood cells, the values of 1,5-anhydroglucitol in whole blood measured by the differential method (Example 4) were correlated well with those measured in Reference Example 4 (correlation coefficient, 0.9974), suggesting that 1,5-anhydroglucitol in whole blood can be measured by the present invention.

Reference Example 5

1) Glucose-Converting Reagent 17.6 mM $MgCl_2$, 17.6 mM KCl, 175.7 mM phosphoenolpyruvate (PEP), 17.6 mM ATP, 123 U/mL pyruvate kinase (PK), and 97 U/mL hexokinase were added to 10.0 mM MES buffer as the composition after the pH was adjusted to 7.0 using 1 N aqueous sodium hydroxide to prepare a glucose-converting reagent.

2) Electrode Reagent Solution

To prepare electrode reagent solutions with two types of compositions, 11.8 mM osmium(III) complex ([Os(III)(bipyridyl)$_2$(imidazoyl)Cl]Cl$_2$), 930 U/mL pyranose oxidase (derived from Basidiomycetous fungi No. 52), and 50 mM 2-sulfobenzoic acid (Reference Example 5-1) or 50 mM 3-sulfobenzoic acid (Reference Example 5-2) were dissolved in purified water in this composition. Preparation of the electrode reagent solution without adding sulfobenzoic acid was designated as Reference Example 5-3.

3) Sensor Chip

A sensor chip for measuring 1,5-anhydroglucitol was prepared by the same manner as in the above 3) of Example 1.

4) Measurement Procedure

Using the sensor chip prepared in the above 3) on day 0 (immediately after preparation) and after stored at room temperature and humidity of approx. 20% for 5 days, 20 μL each of samples containing 1,5-anhydroglucitol 0 μg/mL and 50 μg/mL was mixed with 10 μL of the glucose-converting reagent in Eppendorf tubes and left stand for 5 minutes. Then, 10 μL each of the reaction mixture was applied dropwise on each of the electrodes 11 at the position 1 at which the specimen was applied. 80 seconds later, 0.15 V was applied to the working electrode with respect to the counter electrode for 10 seconds, current values after following 5 seconds were measured with an electrochemical detector. The mean values and the standard deviation of 4 measurements and the change rates are shown in Tables 5-1 and 5-2.

TABLE 5-1

| | 1,5-Anhydroglucitol 0 μg/mL | | | | |
| --- | --- | --- | --- | --- | --- |
| | Day 1 | | Day 5 | | Change rate |
| | Mean (μA) | S.D. | Mean (μA) | S.D. | Day 5/ Day 1 |
| Reference Example 5-1 | 0.77 | 0.06 | 0.96 | 0.03 | 1.24 |
| Reference Example 5-2 | 0.74 | 0.02 | 1.04 | 0.04 | 1.41 |
| Reference Example 5-3 | 1.35 | 0.06 | 3.58 | 0.18 | 2.66 |

TABLE 5-2

| | 1,5-Anhydroglucitol 50 μg/mL | | | | |
| --- | --- | --- | --- | --- | --- |
| | Day 1 | | Day 5 | | Change rate |
| | Mean (μA) | S.D. | Mean (μA) | S.D. | Day 5/ Day 1 |
| Reference Example 5-1 | 1.99 | 0.06 | 2.16 | 0.08 | 1.08 |
| Reference Example 5-2 | 1.89 | 0.02 | 2.21 | 0.04 | 1.17 |
| Reference Example 5-3 | 2.68 | 0.13 | 4.73 | 0.22 | 1.76 |

In Reference Examples 5-1 and 5-2, the change rates (mean current value on day 5/mean current value on day 1) were lower than in Reference Example 5-3, showing that the increase in the current values over time was suppressed. Furthermore, the standard deviation was small, suggesting reliability of measurement, that is, measurement precision was improved. These results demonstrate the effect of addition of a stabilizer to the electrode reagent, which can be applied to electrochemical measurement of 1,5-anhydroglucitol in whole blood.

Example 5

1) Glucose-Converting Reagent

The glucose-converting reagent prepared in 1) of Example 1 was used.

2) Pretreatment Procedure (Common Measurement for 1,5-Anhydroglucitol and Blank)

To create a calibration curve of 1,5-anhydroglucitol, 10 μL each of 4 specimens obtained by adding 1,5-anhydroglucitol preparations with known concentrations (the concentrations of 1,5-anhydroglucitol in the specimens obtained by the procedure in Reference Example 1 except the blood cell separation procedure were 3.8, 7.8, 15.8, and 31.4 μg/mL) to plasma or 4 human whole blood specimens was mixed with 10 μL of the glucose-converting reagent in Eppendorf tubes and left stand for 5 minutes.

3) Procedure Before Electrode Measurement (i) 1,5-Anhydroglucitol Measurement Procedure To the solution after the above-mentioned pretreatment procedure, 5 μL of 100 mM phosphate buffer (pH 7.0) in which 22.0 mM 2,6-dimethylbenzoquinone was dissolved and 5 μL of 100 mM phosphate buffer (pH 7.0) in which 200 U/mL pyranose oxidase (derived from Basidiomycetous fungi No. 52) was dissolved were added successively, mixed, and left stand for 5 minutes.

(ii) Blank Measurement Procedure

To the solution after the above-mentioned pretreatment procedure, 5 μL of 100 mM phosphate buffer (pH 7.0) in which 22.0 mM 2,6-dimethylbenzoquinone was dissolved and 5 μL of 100 mM phosphate buffer (pH 7.0) were added successively, mixed, and left stand for 5 minutes.

4) Measurement Procedure using Sensor Chip

A carbon ink (product name, carbon paste TU15ST: Asahi Chemical Research Laboratory Co., Ltd.) was screen-printed as a working electrode and a lead part, a counter electrode and a lead part, and a reference electrode and a lead part, on a base plate made of polyethylene terephthalate at a thickness of 10

µm and quenched at 150° C. for 40 minutes. Then, a resist ink (product name CR18G-KF: Asahi Chemical Research Laboratory Co., Ltd.) was screen-printed at a thickness of 20 µm except a junction part between the electrode part and a measurement device and quenched at 130° C. for 15 minutes to prepare an electrode 12 shown in FIG. 2.

15 µL each of the reaction mixture obtained in the above 3) was applied dropwise on the electrode 12 at the position 1 at which the specimen was applied, 0.5 V was applied for 10 seconds using the reference electrode as reference, and current values of the sensor chip for measuring 1,5-anhydroglucitol and the sensor chip for measuring a blank after 5 seconds were measured with an electrochemical detector.

5) Calculation of Amounts of 1,5-Anhydroglucitol

A calibration curve was created from the current values obtained by deducting those obtained from the sensor chip for measuring a blank from those obtained from the sensor chip for measuring 1,5-anhydroglucitol by the above-mentioned procedure using specimens for creating a calibration curve of 1,5-anhydroglucitol and the concentrations of 1,5-anhydroglucitol.

For the 4 human whole blood specimens, the current values obtained by deducting those obtained from the sensor chip for measuring a blank from those obtained from the sensor chip for measuring 1,5-anhydroglucitol were similarly compared with the calibration curve to obtain the amounts of 1,5-anhydroglucitol in whole blood. The results are shown in Table 6. The mean values of 4 measurements were used for both the specimens for creation of the calibration curve and the specimens.

Reference Example 6

The same whole blood specimens as measured in Example 5 were measured for 1,5-anhydroglucitol by the same procedure as in Reference Example 1. The results are shown in Table 6.

TABLE 6

| | 1,5-Anhydroglucitol concentration (µg/mL) | |
|---|---|---|
| | Reference Example 6 | Example 5 |
| Whole blood specimen 20 | 16.7 | 17.0 |
| Whole blood specimen 21 | 29.8 | 28.0 |
| Whole blood specimen 22 | 28.9 | 28.6 |
| Whole blood specimen 23 | 31.7 | 31.2 |

When the glucose-converting reagent was allowed to act on whole blood to convert glucose to a substance that does not interfere with measurement and react with the electrode reagent that was not supported on an electrode without separating blood cells, the measured values of 1,5-anhydroglucitol in whole blood (Example 5) were consistent well with those measured by a known measurement method in Reference Example 6 (correlation coefficient, 0.9941), suggesting that 1,5-anhydroglucitol in whole blood can be measured by the present invention.

Reference Example 7

According to the method for evaluating reaction rates of enzymes and mediators described in Denki Kagaku Vol. 63, No. 10, p. 906-911 (1995), reactions of the above-mentioned pyranose oxidase derived from Basidiomycetous fungi No. 52 and the redox mediators listed in Table 7 with 1,5-anhydroglucitol were examined.

A carbon ink (product name, carbon paste TU15ST: Asahi Chemical Research Laboratory Co., Ltd.) was screen-printed on the base plate made of polyethylene terephthalate as a working electrode and a lead part and a counter electrode and a lead part at a thickness of 10 µm, a silver-silver chloride ink (product name, Electrodag PE-409: Acheson) was screen-printed as a reference electrode and a lead part at a thickness of 10 µm, and these were quenched at 150° C. for 40 minutes. Then, a resist ink (product name, CR18G-KF: Asahi Chemical Research Laboratory Co., Ltd.) was screen-printed on a portion except a junction part of the electrode part and the measurement device at a thickness of 20 µm and quenched at 130° C. for 15 minutes to prepare an electrode 13 shown in FIG. 3.

Electrochemical measurement was performed using an electrochemical detector (8-CH Multipotentiostat equipped with function generator FG-02 MODEL PS-08: Toho Giken).

10 µL of an aqueous solution containing 20 U/mL pyranose oxidase and 60 µM of a redox mediator listed in Table 7 was placed on the electrode 13 connected to an electrochemical detector at the position 1 at which the specimen was applied, the potential was swept from −0.5 V to +1 V at 1 mV/sec using the reference electrode of the electrode 13 as reference, and an oxidation current value Id was measured by cyclic voltammentry. Then, 10 µL of an aqueous solution containing 20 U/mL pyranose oxidase, a substrate (500 µg/mL 1,5-anhydroglucitol), and 60 µM of a redox mediator listed in Table 7 was placed on the electrode 13 at the position 1 at which the specimen was applied, the potential was swept from −0.5 V to +1 V at 1 mV/sec using the reference electrode of the electrode 13 as reference, and a catalytic current value Ik was measured by cyclic voltammentry. The rates of reaction of redox mediators with the enzyme were compared by the value Ik/Id obtained by dividing the catalytic current value Ik by the oxidation current value Id with a redox mediator alone.

The results of Ik/Id for each redox mediator are shown in Table 7.

TABLE 7

| Redox mediator | Ik/Id |
|---|---|
| Potassium ferricyanide | 1.7 |
| [Os(III) (bipyridyl)$_2$(imidazoyl)Cl]Cl$_2$ | 14.0 |
| 2,6-Dimethyl-p-benzoquinone | 6.9 |
| 2-Methyl-1,4-naphthoquinone | 2.3 |
| 2,3-Dimethoxy-5-methyl-1,4-benzoquinone | 3.3 |
| N,N-Dimethylaminomethyl ferrocene | 5.1 |
| Ferrocene methanol | 3.4 |
| Thionine acetate | 10.0 |
| Methylene blue | 5.3 |
| Toluidine blue O | 4.1 |
| Azure I | 16.4 |
| Azure C | 5.8 |
| Meldola blue | 1.8 |
| 1-Methoxy-5-methylphenazium methylsulfate | 2.8 |
| 2-Dichlorophenol-indophenol sodium salt dihydrate | 2.8 |
| 4,4'-bis(Dimethylamino)diphenylamine | 3.3 |
| N-Methyl-N-(3-methoxyphenyl)-1,4-phenylenediamine hydrochloride | 2.6 |
| N-Methyl-N-phenyl-1,4-phenylenediamine hydrochloride | 2.5 |
| Nitro-TB* | 1.9 |
| 2,2'-Azinobis(3-ethylbenzothiazoline-6-sulonic acid)diammonium | 1.5 |
| 2-Hydrazono-2,3-dihydro-3-methyl-6-benzothiazole sulfonic acid | 1.2 |

TABLE 7-continued

| Redox mediator | Ik/Id |
|---|---|
| bis-{4-[N-3'-Sulfo-n-propyl-N-n-butyl]amino-2,6-dimethylphenyl}methane | 1.5 |
| bis-{4-[N-3'-Sulfo-n-propyl-N-ethyl]amino-2,6-dimethylphenyl}methane | 1.0 |
| p-Aminophenol | 3.5 |
| N-(3-Sulfopropyl)-3,3',5,5'-tetramethylbenzidine sodium salt | 1.5 |

*Nitro-TB: 3,3'-[3,3'-dimethoxy(1-1'-biphenyl)-4,4'-dyl]-bis[2-(4-nitrophenyl)-5-phenyl-2H-tetrazolium chloride]

Table 7 shows that a pyranose oxidase rapidly reacts with various redox mediators such as osmium complexes, ferrocene compounds, quinone compounds, phenothiazine compounds, phenoxazine compounds, phenazine compounds, diphenylamine compounds, indophenol compounds, and phenol compounds. These results suggest that 1,5-anhydroglucitol in whole blood can be electrochemically measured by methods using these redox mediators and a pyranose oxidase, for example, the methods of Examples 1 to 3.

Reference Example 8

Reactions of the above-mentioned 1,5-anhydroglucitol dehydrogenase and the redox mediators listed in Table 8 were examined by the same manner as in Reference Example 7.

An electrode 13 was prepared by the same manner as in Reference Example 7.

10 μL of an aqueous solution containing 20 U/mL 1,5-anhydroglucitol dehydrogenase (derived from *Pseudomonas* sp. NK-85001) and 60 μM of a redox mediator listed in Table 8 was placed on the electrode 13 connected to an electrochemical detector at the position 1 at which the specimen was applied, the potential was swept from −0.5 V to +1 V at 1 mV/sec using the reference electrode of the electrode 13 as reference, and an oxidation current value Id was measured by cyclic voltammentry. Then, 10 μL of an aqueous solution containing 20 U/mL 1,5-anhydroglucitol dehydrogenase, a substrate (500 μg/mL of 1,5-anhydroglucitol), and 60 μM of a redox mediator listed in Table 8 was placed on the electrode 13 at the position 1 at which the specimen was applied, the potential was swept from −0.5 V to +1 V at 1 mV/sec using the reference electrode of the electrode 13 as reference, and a catalytic current value Ik was measured by cyclic voltammentry. The rates of reactions of redox mediators with the enzyme were compared by the value Ik/Id obtained by the catalytic current value Ik by the oxidation current value Id when a redox mediator alone was contained without a substrate.

The Ik/Id results obtained for each redox mediator are shown in Table 8.

TABLE 8

| Redox mediator | Ik/Id |
|---|---|
| Potassium ferricyanide | 3.4 |
| [Os(III) (bipyridyl)$_2$(imidazoyl)Cl]Cl$_2$ | 18.0 |
| 2,6-Dimethyl-p-benzoquinone | 8.9 |
| 2-Methyl-1,4-naphthoquinone | 64.4 |
| 2,3-Dimethoxy-5-methyl-1,4-benzoquinone | 11.2 |
| N,N-dimethylaminomethyl ferrocene | 5.0 |
| Ferrocene methanol | 4.9 |
| Thionine acetate | 58.8 |
| Methylene blue | 10.9 |
| Toluidine blue O | 21.1 |
| Azure I | 18.3 |
| Azure C | 25.4 |
| New methylene blue | 4.3 |
| 1-Methoxy-5-methylphenazium methylsulfate | 1.6 |
| 2-Dichlorophenol-indophenol sodium salt dihydrate | 10.3 |
| 4,4'-bis(Dimethylamino)diphenylamine | 3.6 |
| N-Methyl-N-(3-methoxyphenyl)-1,4-phenylenediamine hydrochloride | 1.4 |
| N-Methyl-N-phenyl-1,4-phenylenediamine hydrochloride | 2.2 |
| bis-{4-[N-3'-Sulfo-n-propyl-N-n-butyl]amino-2,6-dimethylphenyl}methane | 1.3 |
| p-Aminophenol | 3.2 |
| N-(3-Sulfopropyl)-3,3',5,5'-tetramethylbenzidine sodium salt | 2.2 |
| Malachite green | 2.1 |

Table 8 shows that 1,5-anhydroglucitol dehydrogenase rapidly reacts with various redox mediators such as osmium complexes, ferrocene compounds, quinone compounds, phenothiazine compounds, phenoxazine compounds, phenazine compounds, diphenyl amine compounds, indophenol compounds, and phenol compounds. These results suggest that 1,5-anhydroglucitol in whole blood can be electrochemically measured by methods using these redox mediators and 1,5-anhydroglucitol dehydrogenase, for example, the method of Example 4.

Reference Example 9

1) Glucose-Converting Reagent 14.8 mM MgCl$_2$, 99.2 mM KCl, 48 mM phosphoenolpyruvate (PEP), 2 mM ATP, 20 U/mL pyruvate kinase (PK), 16 U/mL glucokinase, 10 U/mL ascorbic acid oxidase, 200 mM sodium chloride, 0.2 mM EDTA •2Na, and 1.2 g/L BSA were added to 50 mM MES buffer as the composition after the pH was adjusted to 7.0 using 1 N aqueous sodium hydroxide to prepare a glucose-converting reagent.

2) Electrode Reagent Solutions

To prepare electrode reagent solutions (a), (b), and (c),
(a) 0.54 mM ferrocenyl PEG(Dojindo Laboratories);
(b) 6.25 U/mL horseradish peroxidase (Toyobo Co., Ltd.); or
(c) 50 U/mL pyranose oxidase (derived from Basidiomycetous fungi No. 52)
was dissolved in 100 mM MES buffer (pH 7.0) in this composition.

3) Sensor Chip

First, 10 μL of 0.5% aqueous carboxymethylcellulose was applied to the working electrode site of the electrode 13 prepared in Reference Example 7 and dried at 50° C. for 10 minutes to make the electrode surface hydrophilic. Then, 3 μL of the electrode reagent solution (a) obtained in the above 2) was applied dropwise in the hydrophilic part and dried, 3 μL of the electrode reagent solution (b) was applied dropwise thereon and dried, and then 3 μL of the electrode reagent solution (c) was further applied dropwise and dried to prepare a sensor chip.

4) Creation of Calibration Curve

To create a calibration curve of 1,5-anhydroglucitol, 20 μL each of 3 specimens obtained by adding 1,5-anhydroglucitol preparations with known concentrations (the concentrations of 1,5-anhydroglucitol in the specimens obtained by the procedure in Reference Example 1 except the blood cell separation procedure were 0, 10, and 50 μg/mL) to physiological saline and 10 μL of the glucose-converting reagent were mixed in Eppendorf tubes and left stand for 5 minutes. Then, 15 μL each of the reaction mixture was applied dropwise on the electrode 13 of the sensor chip of 3) at the position 1 at which the specimen was applied and reacted for 5 minutes, then 0 V was applied using the reference electrode (silver-silver chloride) as reference, and current values after 5 seconds were measured with an electrochemical detector. A calibration curve was created from the current values and the concentrations of 1,5-anhydroglucitol as shown in FIG. 4. In the figure, 1,5AG denotes 1,5-anhydroglucitol.

The obtained calibration curve shows a calibration curve with favorable concentration dependence. These results suggest that 1,5-anhydroglucitol in whole blood can be electrochemically measured by methods using ferrocenyl PEG and pyranose oxidase, for example, the methods of Examples 1 to 3.

Reference Example 10

1) Glucose-Converting Reagent

The glucose-converting reagent in 1) of Example 1 was used.

2) Electrode Reagent Solutions

Redox mediators having concentrations in Table 9 and 1,5-anhydroglucitol dehydrogenase (derived from *Pseudomonas* sp. NK-85001) having concentrations in Table 9 were dissolved purified water in each composition to prepare an electrode reagent solution.

3) Sensor Chip

2 μL of an electrode reagent solution obtained in the above 2) was applied to the working electrode of the electrode 13 prepared in Reference Example 7 and dried at 50° C. for 5 minutes to prepare a sensor chip.

4) Creation of Calibration Curves

To create a calibration curve of 1,5-anhydroglucitol, 10 μL each of 5 specimens obtained by adding 1,5-anhydroglucitol preparations with known concentrations (the concentrations of 1,5-anhydroglucitol in the specimens obtained by the procedure in Reference Example 1 except the blood cell separation procedure were 0, 2.5, 11.9, 24.2, and 49.3 μg/mL) to 0.38% sodium citrate solution and 5 μL of the glucose-converting reagent were mixed in Eppendorf tubes and left stand for 5 minutes. Then, 10 μL each of the reaction mixture was applied dropwise on the electrode 13 at the position 1 at which the specimen was applied, each of the potentials listed in Table 9 was applied using the reference electrode (silver-silver chloride) as reference, current values after 5 seconds were measured with an electrochemical detector, and a calibration curve was created from the current values and the concentrations of 1,5-anhydroglucitol. These calibration curves are shown in FIGS. 5 to 13.

TABLE 9

| Test No. | Redox mediator | Mediator concentration in electrode reagent solution (μM) | AGDH* concentration in electrode reagent solution (U/mL) | Potential |
|---|---|---|---|---|
| No. 1 | 2,6-Dimethyl-p-benzoquinone | 150 | 50 | 0.5 |
| No. 2 | 2-Methyl-1,4-naphthoquinone | 150 | 50 | 0.1 |
| No. 3 | Thionine chloride | 75 | 50 | −0.1 |
| No. 4 | Methylene blue | 200 | 100 | −0.2 |
| No. 5 | Toluidine blue O | 12.5 | 50 | −0.1 |
| No. 6 | Azure C | 75 | 50 | 0 |
| No. 7 | 4,4'-bis(Dimethylamino)-diphenylamine | 75 | 50 | 0 |
| No. 8 | 2-Dichlorophenol-indophenol sodium salt dihydrate | 75 | 50 | 0.1 |
| No. 9 | 1-Methoxy-5-methylphenazium methylsulfate | 150 | 50 | 0 |

*AGDH, 1,5-anhydroglucitol dehydrogenase

The obtained calibration curves are all concentration-dependent smooth calibration curves. These results suggest that 1,5-anhydroglucitol in whole blood can be electrochemically measured by amperometry using these mediators and 1,5-anhydroglucitol dehydrogenase.

Reference Example 11

1) Glucose-Converting Reagent

The glucose-converting reagent obtained in 1) of Example 1 was used.

2) Electrode Reagent Solution

The redox mediators having concentrations listed in Table 10 and 1,5-anhydroglucitol dehydrogenase having concentrations listed in Table 10 (derived from *Pseudomonas* sp. NK-85001) were dissolved in purified water in each composition to prepare an electrode reagent solution.

3) Sensor Chip

2 μL of an electrode reagent solution of the above 2) was applied to the working electrode of the electrode 13 prepared in Reference Example 7 and dried at 50° C. for 5 minutes to prepare a sensor chip.

4) Creation of Calibration Curve

To create a calibration curve of 1,5-anhydroglucitol, 10 μL each of 6 specimens obtained by adding 1,5-anhydroglucitol preparations at known concentrations (the concentrations of 1,5-anhydroglucitol in the specimens obtained by the procedure in Reference Example 1 except the blood cell separation procedure were 0, 2.5, 5.0, 11.9, 24.2, and 49.3 μg/mL) to 0.38% sodium citrate solution and 5 μL of the glucose-converting reagent were mixed in Eppendorf tubes and left stand for 5 minutes. Then, 10 μL each of the reaction mixture was applied dropwise on the electrode 13 at the position 1 at which the specimen was applied, each of the first potentials in Table 10 was applied for 10 seconds using the reference electrode (silver-silver chloride) as reference, and then the second potential was applied for 110 seconds using the reference electrode (silver-silver chloride) as reference. Coulomb levels for 100 seconds from the start of application of the second potential were measured with an electrochemical detector for coulometry, and a calibration curve was created from the coulomb levels and the concentrations of 1,5-anhydroglucitol. The calibration curves are shown in FIGS. 14 to 27.

dure in Reference Example 1 except the blood cell separation procedure were 0, 2.5, 5.0, 11.9, 24.2, 49.3, and 98.8 µg/mL) to 0.38% sodium citrate solution and 5 µL of the glucose-converting reagent were mixed in Eppendorf tubes and left stand for 5 minutes. Then, 10 µL each of the reaction mixture was applied dropwise on the electrode 13 at the position 1 at

TABLE 10

| Test No. | Redox mediator | Mediator concentration in electrode reagent solution (µM) | AGDH concentration in electrode reagent solution (µM) | First potential | Second potential |
|---|---|---|---|---|---|
| No. 1 | [Os(III) (bipyridyl)$_2$(imidazoyl)Cl]Cl$_2$ | 300 | 25 | 0.15 | 0.25 |
| No. 2 | 2,6-Dimethyl-p-benzoquinone | 150 | 50 | 0.5 | 0.6 |
| No. 3 | 2,3-Dimethoxy-5-methyl-1,4-benzoquinone | 150 | 50 | 0.5 | 0.6 |
| No. 4 | 2-Methyl-1,4-naphthoquinone | 150 | 50 | 0.1 | 0.2 |
| No. 5 | Thionine acetate | 5 | 50 | −0.1 | 0 |
| No. 6 | Thionine chloride | 75 | 50 | −0.1 | 0 |
| No. 7 | Methylene blue | 200 | 100 | −0.2 | −0.1 |
| No. 8 | Toluidine blue O | 12.5 | 50 | −0.1 | 0 |
| No. 9 | Azure I | 120 | 40 | 0.2 | 0.3 |
| No. 10 | Azure C | 75 | 50 | 0 | 0.1 |
| No. 11 | Meldola blue | 150 | 50 | 0 | 0.1 |
| No. 12 | 4,4'-bis(Dimethylamino)-diphenylamine | 75 | 50 | 0 | 0.1 |
| No. 13 | 2-Dichlorophenol-indophenol sodium salt dihydrate | 75 | 50 | 0.1 | 0.2 |
| No. 14 | 1-Methoxy-5-methylphenazium methylsulfate | 150 | 50 | 0 | 0.1 |

* AGDH, 1,5-anhydroglucitol dehydrogenase

The obtained calibration curves are all concentration-dependent smooth calibration curves. These results suggest that 1,5-anhydroglucitol in whole blood can be electrochemically measured by coulometry using these mediators and 1,5-anhydroglucitol dehydrogenase.

Example 6

1) Glucose-Converting Reagent

The glucose-converting reagent obtained in 1) of Example 1 was used.

2) Electrode Reagent Solution

120 µM thionine acetate (Sigma-Aldrich Japan K.K.) and 40 U/mL 1,5-anhydroglucitol dehydrogenase (derived from *Pseudomonas* sp. NK-85001) were dissolved in purified water in this composition to prepare an electrode reagent solution.

3) Sensor Chip

2 µL of the electrode reagent solution obtained in the above 2) was applied to the working electrode of the electrode 13 prepared in Reference Example 7 and dried at 50° C. for 5 minutes to prepare sensor chip.

4) Creation of Calibration Curve

To create a calibration curve of 1,5-anhydroglucitol, 10 µL each of 7 specimens obtained by adding 1,5-anhydroglucitol preparations at known concentrations (the concentrations of 1,5-anhydroglucitol in the specimens obtained by the procedure in Reference Example 1 except the blood cell separation procedure were 0, 2.5, 5.0, 11.9, 24.2, 49.3, and 98.8 µg/mL) to 0.38% sodium citrate solution and 5 µL of the glucose-converting reagent were mixed in Eppendorf tubes and left stand for 5 minutes. Then, 10 µL each of the reaction mixture was applied dropwise on the electrode 13 at the position 1 at which the specimen was applied, and −0.1 V was applied for 10 seconds, followed by 0 V for 110 seconds, using the reference electrode (silver-silver chloride) as reference. Coulomb levels were measured with an electrochemical detector for 100 seconds from the start of application of 0 V, and a calibration curve was created from the coulomb levels and the concentrations of 1,5-anhydroglucitol. A calibration curve showing favorable linearity is shown in FIG. 28.

5) 1,5-Anhydroglucitol Measurement Procedure

10 µL each of human whole blood specimens from 7 subjects for measuring 1,5-anhydroglucitol and 5 µL of the glucose-converting reagent were mixed in Eppendorf tubes and left stand for 5 minutes. Then, 10 µL each of the reaction mixture was applied dropwise on the electrode 13 at the position 1 at which the specimen was applied, and −0.1 V was applied for 10 seconds, followed by 0 V for 110 seconds, using the reference electrode (silver-silver chloride) as reference. Coulomb levels were measured with an electrochemical detector for 100 seconds from the start of application of 0 V and compared with the calibration curve to obtain the amounts of 1,5-anhydroglucitol in the 7 whole blood specimens. The results are shown in Table 11. The results are the mean values of 4 measurements.

Reference Example 12

For comparison, the same whole blood specimens as measured in 5) of Example 6 were measured for 1,5-anhydroglucitol by the procedure in Reference Example 1. The results are shown in Table 11.

TABLE 11

| | 1,5-Anhydroglucitol concentration (μg/mL) | |
|---|---|---|
| | Reference Example 12 | Example 6 |
| Whole blood specimen 24 | 8.5 | 10.1 |
| Whole blood specimen 25 | 15.7 | 15.2 |
| Whole blood specimen 26 | 12.9 | 12.1 |
| Whole blood specimen 27 | 22.7 | 19.0 |
| Whole blood specimen 28 | 25.6 | 24.5 |
| Whole blood specimen 29 | 26.8 | 21.5 |
| Whole blood specimen 30 | 28.5 | 26.3 |

When the glucose-converting reagent was allowed to act on whole blood to convert glucose to a substance that does not interfere with measurement and reacted with the electrode reagent containing thionine acetate without separating blood cells, the measured values of 1,5-anhydroglucitol in whole blood (Example 6) were consistent well with those measured in Reference Example 12 by a known measurement method (correlation coefficient, 0.9711), suggesting that 1,5-anhydroglucitol in whole blood can be electrochemically measured by the present invention.

Example 7

1) Glucose-Converting Reagent

The glucose-converting reagent obtained in 1) of Example 1 was used.

2) Electrode Reagent Solutions (i) For measuring 1,5-Anhydroglucitol
50 μM methylene blue (Yoneyama Yakuhin Kogyo Co., Ltd.) and 100 U/mL 1,5-anhydroglucitol dehydrogenase (derived from *Pseudomonas* sp. NK-85001) were dissolved in purified water in this composition to prepare an electrode reagent solution.
(ii) For Measuring Blank
50 μM methylene blue (Yoneyama Yakuhin Kogyo Co., Ltd.) was dissolved in purified water in this composition to prepare an electrode reagent solution.

3) Sensor Chips

2 μL of the electrode reagent solution for measuring 1,5-anhydroglucitol or for measuring a blank obtained in the above 2) was applied to the working electrode of the two electrodes 13 shown in FIG. 3 prepared in Reference Example 7 and dried at 50° C. for 5 minutes to prepare a sensor chip for measuring 1,5-anhydroglucitol or for measuring a blank.

4) Creation of Calibration Curve

To create a calibration curve of 1,5-anhydroglucitol, 20 μL each of 6 specimens obtained by adding 1,5-anhydroglucitol preparations at known concentrations (the concentrations of 1,5-anhydroglucitol in the specimens obtained by the procedure in Reference Example 1 except the blood cell separation procedure were 0.6, 2.8, 5.0, 10.0, 24.7, and 50.2 μg/mL) to sheep serum (Nippon Bio Test Lab.), which is known to contain virtually no 1,5-anhydroglucitol, and 10 μL of the glucose-converting reagent were mixed in Eppendorf tubes and left stand for 5 minutes. Then, 10 μL each of the reaction mixture was applied dropwise on the electrode 13 of the sensor chip for measuring 1,5-anhydroglucitol or for measuring a blank at the position 1 at which the specimen was applied, and −0.2 V was applied for 10 seconds, followed by −0.1 V for 110 seconds using the reference electrode (silver-silver chloride) of each sensor chip as reference. Coulomb levels were measured with an electrochemical detector for 100 seconds from the start of application of −0.1 V. A calibration curve was created from the coulomb levels obtained by deducting those of the sensor chip for measuring a blank from those of the sensor chip for measuring 1,5-anhydroglucitol and the concentrations of 1,5-anhydroglucitol. The calibration curve showing favorable linearity is shown in FIG. 29.

5) 1,5-Anhydroglucitol Measurement Procedure

20 μL each of whole blood from the 7 subjects in Example 6 and 10 μL of the glucose-converting reagent were mixed in Eppendorf tubes and left stand for 5 minutes. Then, 10 μL each of the reaction mixture was applied dropwise on the electrode 13 of the sensor chip for measuring 1,5-anhydroglucitol or for measuring a blank at the position 1 at which the specimen was applied, and −0.2 V was applied for 10 seconds, followed by −0.1 V for 110 seconds, using the reference electrode (silver-silver chloride) of each sensor chip as reference. Coulomb levels were measured for 100 seconds from the start of application of −0.1 V with an electrochemical detector (8-CH Multipotentiostat MODEL PS-08 equipped with GPIB RS232C: Toho Giken), and the coulomb levels obtained by deducting those of the sensor chip for measuring a blank from those of the sensor chip for measuring 1,5-anhydroglucitol were compared with the calibration curve to obtain the amounts of 1,5-anhydroglucitol in the 7 whole blood specimens. The results are shown in Table 12. The results are the mean values of 4 measurements.

Reference Example 12

Since the specimens used in Example 7 were the same whole blood specimens as in Example 6, the results of Example 6 are shown as Reference Example 12 in Table 12.

TABLE 12

| | 1,5-Anhydroglucitol concentration (μg/mL) | |
|---|---|---|
| | Reference Example 12 | Example 7 |
| Whole blood specimen 24 | 8.5 | 9.6 |
| Whole blood specimen 25 | 15.7 | 14.5 |
| Whole blood specimen 26 | 12.9 | 12.9 |
| Whole blood specimen 27 | 22.7 | 23.7 |
| Whole blood specimen 28 | 25.6 | 20.9 |
| Whole blood specimen 29 | 26.8 | 23.9 |
| Whole blood specimen 30 | 28.5 | 24.1 |

When the glucose-converting reagent was allowed to act on whole blood to convert glucose to a substance that does not interfere with measurement and reacted with the electrode reagent containing methylene blue without separating blood cells, the measured values of 1,5-anhydroglucitol in whole blood (Example 7) were consistent well with those measured in Reference Example 12 by a known measurement method (correlation coefficient, 0.9658), suggesting that 1,5-anhydroglucitol in whole blood can be electrochemically measured by the present invention.

Example 8

1) Glucose-Converting Reagent

The glucose-converting reagent obtained in 1) of Example 1 was used.

2) Electrode Reagent Solution

120 μM thionine acetate (Sigma-Aldrich Japan K.K.) and 40 U/mL 1,5-anhydroglucitol dehydrogenase (derived from *Pseudomonas* sp. NK-85001) were dissolved in purified water in this composition to prepare an electrode reagent solution.

3) Sensor Chip

2 μL of the electrode reagent solution obtained in the above 2) was applied to the working electrode of the electrode 13 prepared in Reference Example 7 and dried at 50° C. for 5 minutes to prepare a sensor chip.

4) Creation of Calibration Curve

To create a calibration curve of 1,5-anhydroglucitol, 10 μL each of 7 specimens obtained by adding 1,5-anhydroglucitol preparations at known concentrations (the concentrations of 1,5-anhydroglucitol in the specimens obtained by the procedure in Reference Example 1 except the blood cell separation procedure were 0.6, 2.8, 5.0, 10.0, 24.7, 50.2, and 103.9 μg/mL) to sheep serum (Nippon Bio Test Labo.) and 5 μL of the glucose-converting reagent were mixed in Eppendorf tubes and left stand for 5 minutes. Then, 10 μL each of the reaction mixture was applied dropwise on the electrode 13 at the position 1 at which the specimen was applied, −0.1 V was applied using the reference electrode (silver-silver chloride) as reference, current values after 5 seconds were measured with an electrochemical detector, and a calibration curve was created from the current values and the concentrations of 1,5-anhydroglucitol. A calibration curve showing favorable linearity is shown in FIG. 30.

5) 1,5-Anhydroglucitol Measurement Procedure

10 μL each of whole blood from the 7 subjects in Example 6 and 5 μL of the glucose-converting reagent were mixed in Eppendorf tubes and left stand for 5 minutes. Then, 10 μL each of the reaction mixture was applied dropwise on the electrode 13 at the position 1 at which the specimen was applied, −0.1 V was applied using the reference electrode (silver-silver chloride) as reference, current values after 5 seconds were measured with an electrochemical detector, and the obtained current values were compared with the calibration curve to obtain the amounts of 1,5-anhydroglucitol in 7 whole blood specimens. The results are shown in Table 13. The results are the mean values of 4 measurements.

Reference Example 12

Since the specimens used in Example 8 were the same whole blood specimens as in Example 6, the measurement results of Example 6 are shown as Reference Example 12 in Table 13.

TABLE 13

| | 1,5-Anhydroglucitol concentration (μg/mL) | |
|---|---|---|
| | Reference Example 12 | Example 8 |
| Whole blood specimen 24 | 8.5 | 10.0 |
| Whole blood specimen 25 | 15.7 | 14.7 |
| Whole blood specimen 26 | 12.9 | 11.7 |
| Whole blood specimen 27 | 22.7 | 19.5 |
| Whole blood specimen 28 | 25.6 | 25.4 |
| Whole blood specimen 29 | 26.8 | 21.6 |
| Whole blood specimen 30 | 28.5 | 27.0 |

When the glucose-converting reagent was allowed to act on whole blood to convert glucose to a substance that does not interfere with measurement and reacted with the electrode reagent containing thionine acetate without separating blood cells, the measured values of 1,5-anhydroglucitol in whole blood (Example 8) were consistent well with those measured in Reference Example 12 by a known measurement method (correlation coefficient, 0.9700), suggesting that 1,5-anhydroglucitol in whole blood can be electrochemically measured by the present invention.

Example 9

1) Glucose-Converting Reagent

The glucose-converting reagent obtained in 1) of Example 1 was used.

2) Electrode Reagent Solution

120 μM thionine acetate (Sigma-Aldrich Japan K.K.) and 40 U/mL 1,5-anhydroglucitol dehydrogenase (derived from *Pseudomonas* sp. NK-85001) were dissolved in purified water in this composition to prepare an electrode reagent solution.

3) Sensor Chip

2 μL of the electrode reagent solution obtained in the above 2) was applied to the working electrode of the electrode 13 that was prepared in Reference Example 7 and treated by the same manner as in Reference Example 9 and dried at 50° C. for 5 minutes to prepare a sensor chip.

4) Creation of Calibration Curve

To create a calibration curve of 1,5-anhydroglucitol, 10 μL each of 4 specimens obtained by adding 1,5-anhydroglucitol preparations at known concentrations (the concentrations of 1,5-anhydroglucitol in the specimens obtained by the procedure in Reference Example 1 except the blood cell separation procedure were 0, 5.0, 11.9, and 24.2 μg/mL) to 0.38% sodium citrate solution and 5 μL of the glucose-converting reagent were mixed in Eppendorf tubes and left stand for 5 minutes. Then, 10 μL each of the reaction mixture was applied dropwise on the electrode 13 at the position 1 at which the specimen was applied, 0 V was applied for 110 seconds using the reference electrode (silver-silver chloride) as reference, coulomb levels were measured with an electrochemical detector for 100 seconds from the start of application, and a calibration curve was created from the coulomb levels of the sensor chip and the concentrations of 1,5-anhydroglucitol. The calibration curve having favorable linearity is shown in FIG. 31.

5) 1,5-Anhydroglucitol Measurement Procedure

10 μL each of human whole blood from 6 subjects for measuring 1,5-anhydroglucitol and 5 μL of the glucose-converting reagent were mixed in Eppendorf tubes and left stand for 5 minutes. Then, 10 μL each of the reaction mixture was applied dropwise on the electrode 13 at the position 1 at which the specimen was applied, 0 V was applied for 110 seconds using the reference electrode (silver-silver chloride) as reference, coulomb levels were measured with an electrochemical detector for 100 seconds from the start of application, and the obtained coulomb levels were compared with the calibration curve to obtain the amounts of 1,5-anhydroglucitol in the 6 whole blood specimens. The results are shown in Table 14. The results are the mean values of 4 measurements.

Reference Example 13

For comparison, the same whole blood specimens as measured in 5) of Example 9 were measured for 1,5-anhydroglucitol by the procedure in Reference Example 1. The results are shown in Table 14.

TABLE 14

|  | 1,5-Anhydroglucitol concentration (μg/mL) | |
| --- | --- | --- |
|  | Reference Example 13 | Example 9 |
| Whole blood specimen 31 | 8.9 | 10.6 |
| Whole blood specimen 32 | 16.2 | 15.2 |
| Whole blood specimen 33 | 14.1 | 14.0 |
| Whole blood specimen 34 | 23.3 | 21.3 |
| Whole blood specimen 35 | 25.9 | 23.1 |
| Whole blood specimen 36 | 32.1 | 24.7 |

When the glucose-converting reagent was allowed to act on whole blood to convert glucose to a substance that does not interfere with measurement and reacted with the electrode reagent containing thionine acetate without separating blood cells, the measured values of 1,5-anhydroglucitol in whole blood (Example 9) were consistent well with the measured value in Reference Example 13 by a known measurement method (correlation coefficient, 0.9855), suggesting that 1,5-anhydroglucitol in whole blood can be electrochemically measured by the present invention.

Example 10

1) Glucose-Converting Reagent

The glucose-converting reagent obtained in 1) of Example 1 was used.

2) Electrode Reagent Solutions (i) For measuring 1,5-anhydroglucitol
100 μM methylene blue (Tokyo Kasei Kogyo) and 50 U/mL 1,5-anhydroglucitol dehydrogenase (derived from *Pseudomonas* sp. NK-85001) were dissolved in purified water in this composition to prepare an electrode reagent solution.

(ii) For Measuring Blank
100 μM methylene blue (Tokyo Kasei Kogyo) was dissolved in purified water in this composition to prepare electrode reagent solution.

3) Sensor Chips

The two electrodes 13 prepared in Reference Example 7 and shown in FIG. 3 were prepared, 2 μL of the electrode reagent solution for measuring 1,5-anhydroglucitol or for measuring a blank obtained in the above 2) was applied to the working electrode of the electrode and dried at 50° C. for 5 minutes to prepare a sensor chip for measuring 1,5-anhydroglucitol or for measuring a blank.

4) Creation of Calibration Curve

To create a calibration curve of 1,5-anhydroglucitol, 20 μL each of 4 specimens obtained by adding 1,5-anhydroglucitol preparations at known concentrations (the concentrations of 1,5-anhydroglucitol in the specimens obtained by the procedure in Reference Example 1 except the blood cell separation procedure were 0.6, 10.0, 50.2, and 103.9 μg/mL) to sheep serum (Nippon Bio Test Lab.) and 10 μL of the glucose-converting reagent were mixed in Eppendorf tubes and left stand for 5 minutes. Then, 10 μL each of the reaction mixture was applied dropwise on the electrode 13 of the sensor chip for measuring 1,5-anhydroglucitol or for measuring a blank at the position 1 at which the specimen was applied, −0.1 V was applied for 110 seconds using the reference electrode (silver-silver chloride) of the sensor chip as reference, and coulomb levels were measured with an electrochemical detector for 100 seconds from the start of application of −0.1 V. A calibration curve was created from differences between the coulomb levels obtained from the sensor chip for measuring 1,5-anhydroglucitol and those obtained from the sensor chip for measuring a blank, and the concentration of 1,5-anhydroglucitol. The calibration curve having favorable linearity is shown in FIG. 32.

5) 1,5-Anhydroglucitol Measurement Procedure

20 μL each of whole blood from the 6 subjects in Example 9 and 10 μL of the glucose-converting reagent were mixed in Eppendorf tubes and left stand for 5 minutes. Then, 10 μL each of the reaction mixture was applied dropwise on the electrode 13 of the sensor chip for measuring 1,5-anhydroglucitol or for measuring a blank at the position 1 at which the specimen was applied, −0.1 V was applied for 110 seconds using the reference electrode (silver-silver chloride) of the sensor chip as reference, coulomb levels were measured with an electrochemical detector for 100 seconds from the start of application of −0.1 V, and the coulomb levels obtained by deducting those of the sensor chip for measuring a blank from those of the sensor chip for measuring 1,5-anhydroglucitol were compared with the calibration curve to obtain the amounts of 1,5-anhydroglucitol in the 6 whole blood specimens. The results are shown in Table 15. The results are the mean values of 4 measurements.

Reference Example 13

Since the specimens used in Example 10 were the same whole blood specimens as used in Example 9, the measurement results of Example 9 are shown as Reference Example 13 in Table 15.

TABLE 15

|  | 1,5-Anhydroglucitol concentration (μg/mL) | |
| --- | --- | --- |
|  | Reference Example 13 | Example 10 |
| Whole blood specimen 31 | 8.9 | 11.0 |
| Whole blood specimen 32 | 16.2 | 17.2 |
| Whole blood specimen 33 | 14.1 | 15.0 |
| Whole blood specimen 34 | 23.3 | 24.0 |
| Whole blood specimen 35 | 25.9 | 24.5 |
| Whole blood specimen 36 | 32.1 | 31.4 |

When the glucose-converting reagent was allowed to act on whole blood to convert glucose to a substance that does not interfere with measurement and reacted with the electrode reagent containing methylene blue without separating blood cells, the measured values of 1,5-anhydroglucitol in whole blood (Example 10) as measured by a differential method were consistent well with those measured in Reference Example 13 by a known measurement method (correlation coefficient, 0.9964), suggesting that 1,5-anhydroglucitol in whole blood can be electrochemically measured by the present invention.

INDUSTRIAL APPLICABILITY 1,5-Anhydroglucitol in a trace amount whole blood can be measured by the method for measuring 1,5-anhydroglucitol of the present invention which electrochemically measures 1,5-anhydroglucitol without using a centrifuge and the like. Therefore, the measurement method of the present invention can be applied to rapid measurement of 1,5-anhydroglucitol at bedside or in a clinic and measurement by patients themselves at home.

DESCRIPTION OF REFERENCE NUMERALS

Figure 1:
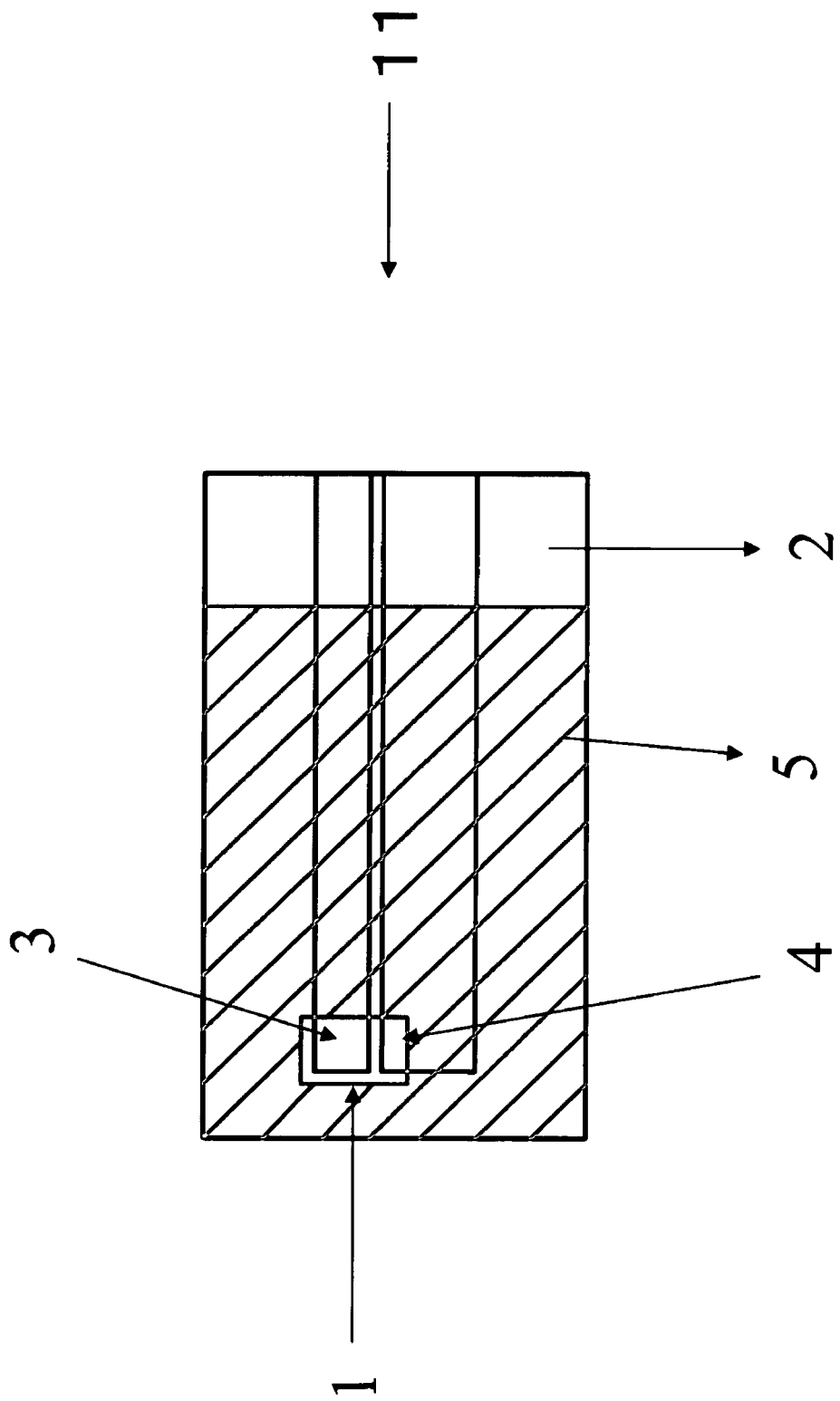
FIG. 1 is a simplified diagram showing an electrode 11 used in the present invention.
Figure 2:
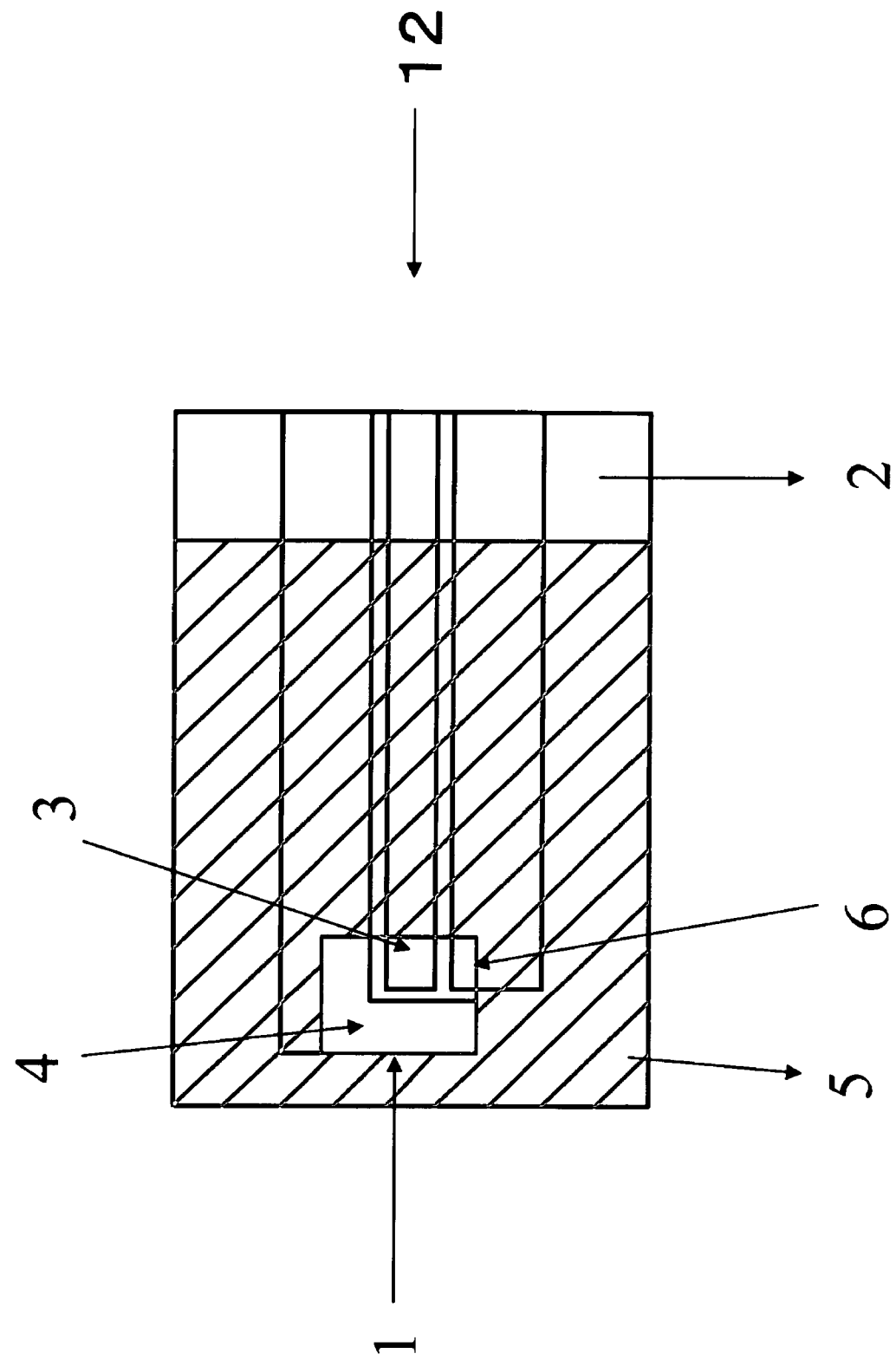
FIG. 2 is a simplified diagram showing an electrode 12 used in the present invention.
Figure 3:
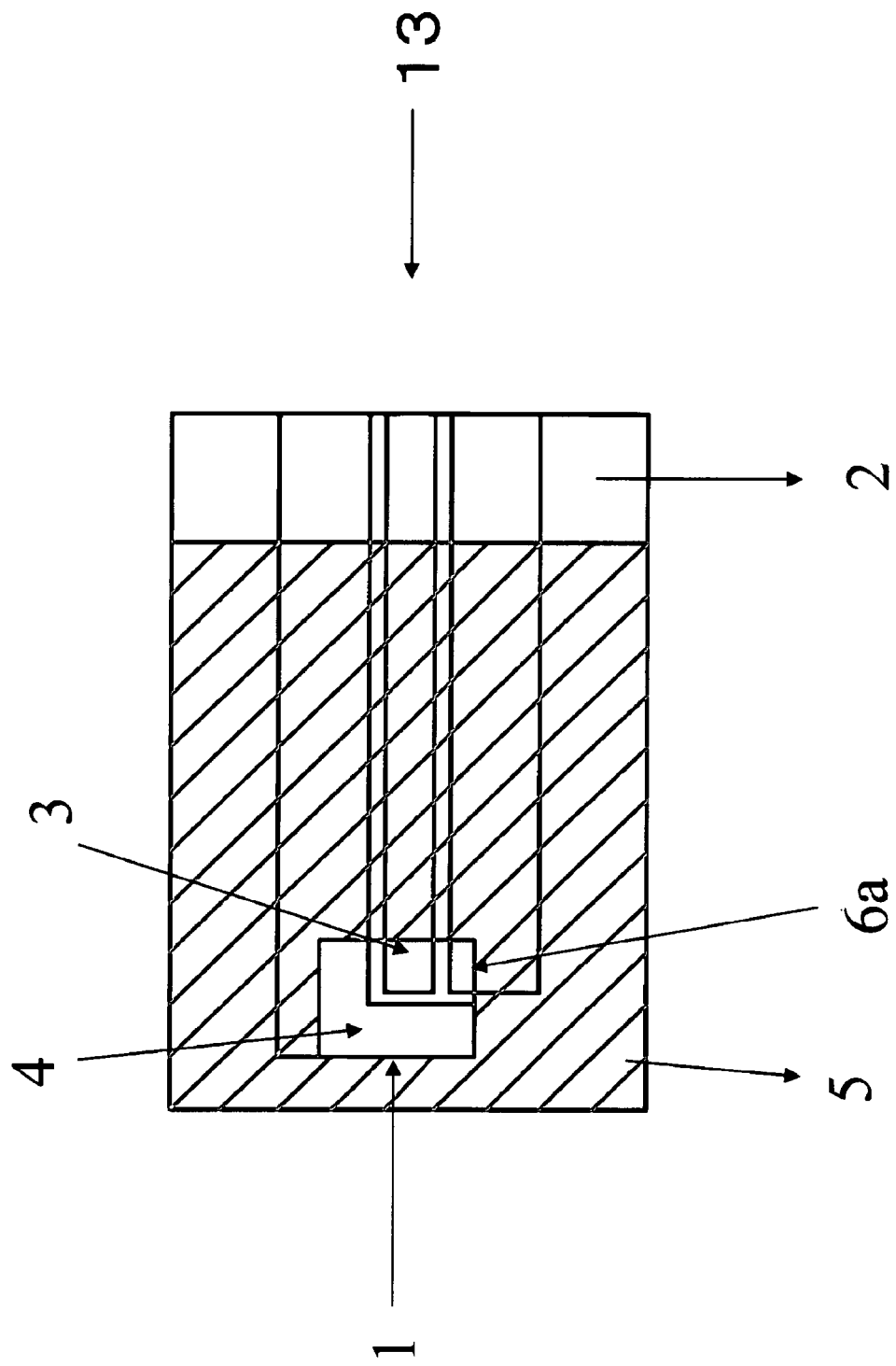
FIG. 3 is a simplified diagram showing an electrode 13 used in the present invention.
Figure 4:
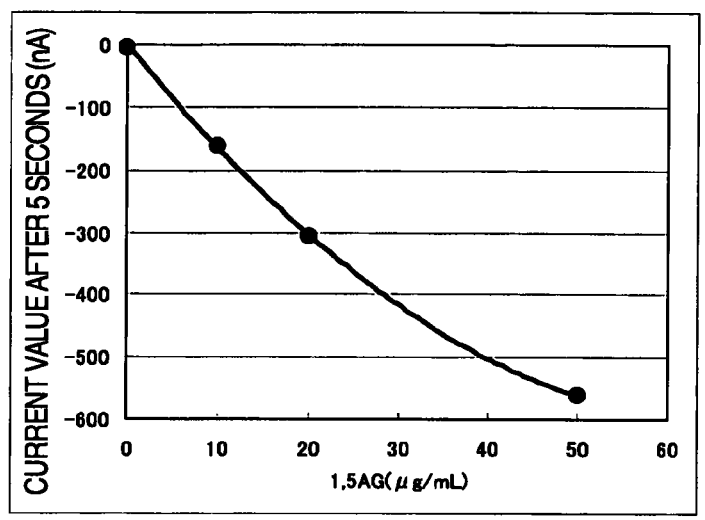
FIG. 4 is a calibration curve created in Reference Example 9.
Figure 5:
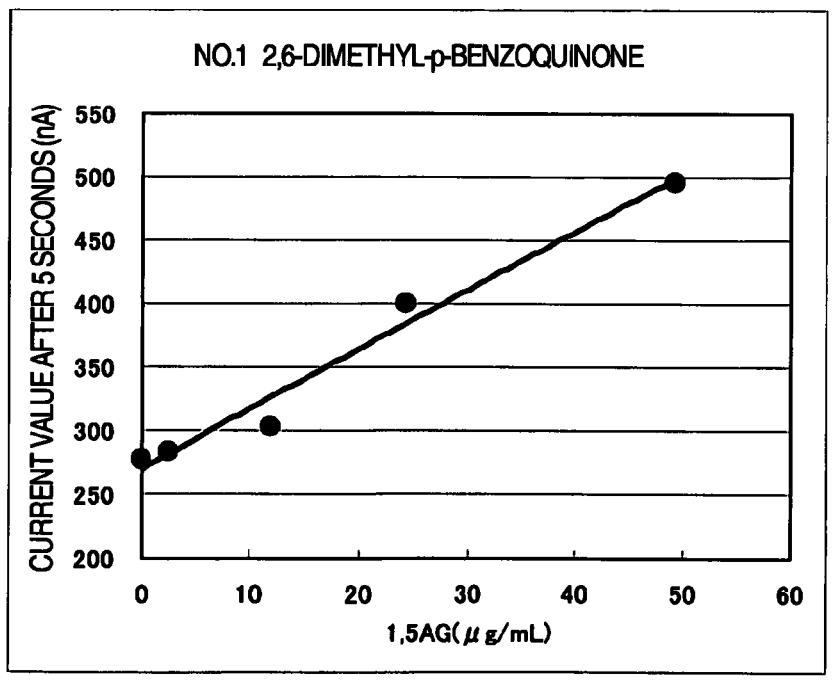
FIG. 5 is a calibration curve of Test No. 1 in Table 9 in Reference Example 10.
Figure 6:
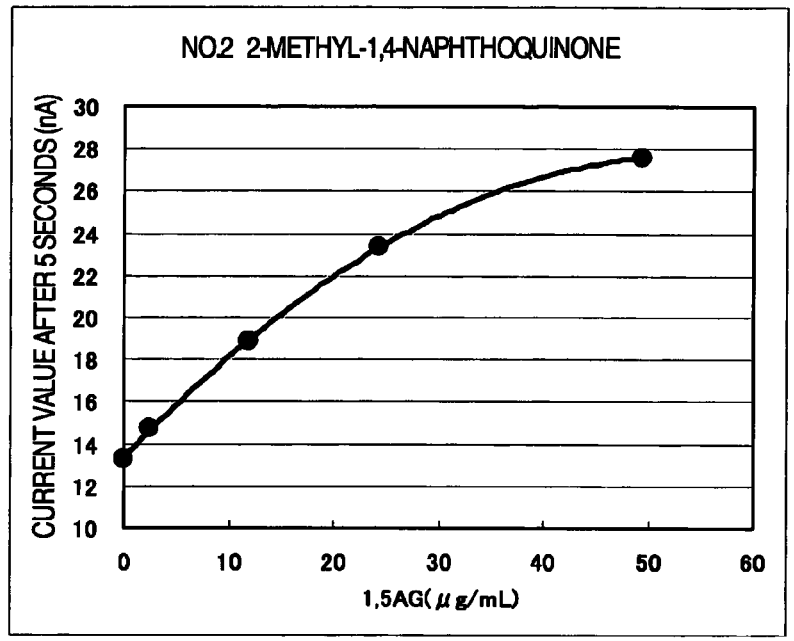
FIG. 6 is a calibration curve of Test No. 2 in Table 9 in Reference Example 10.
Figure 7:
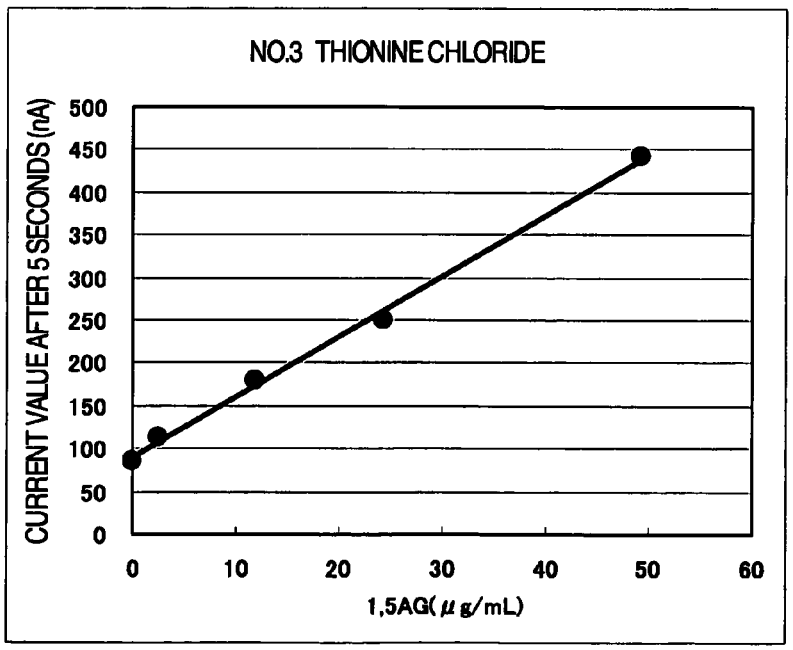
FIG. 7 is a calibration curve of Test No. 3 in Table 9 in Reference Example 10.
Figure 8:
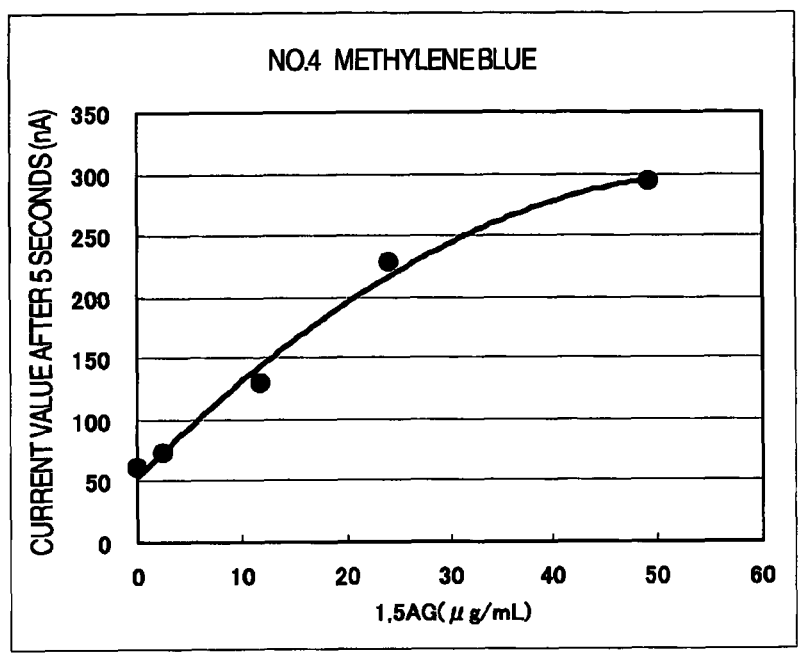
FIG. 8 is a calibration curve of Test No. 4 in Table 9 in Reference Example 10.
Figure 9:
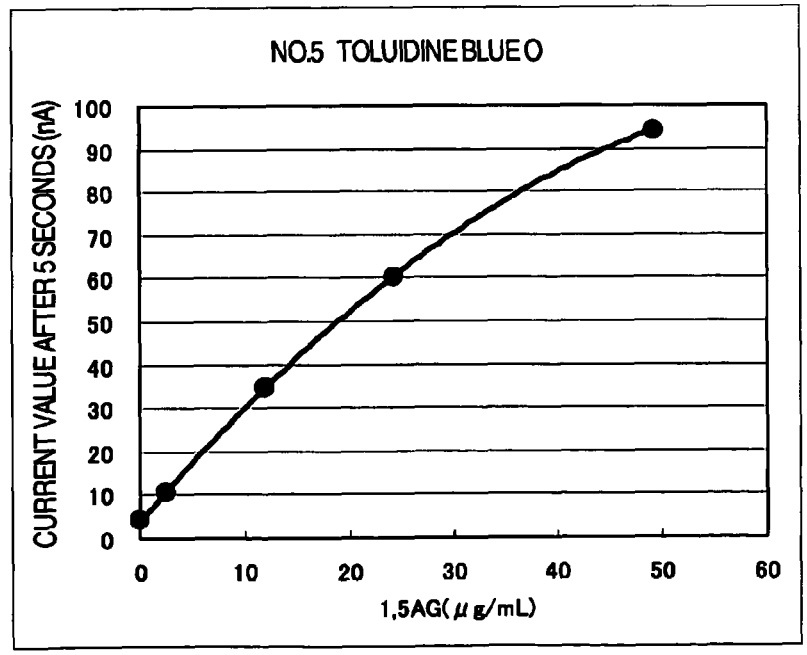
FIG. 9 is a calibration curve of Test No. 5 in Table 9 in Reference Example 10.
Figure 10:
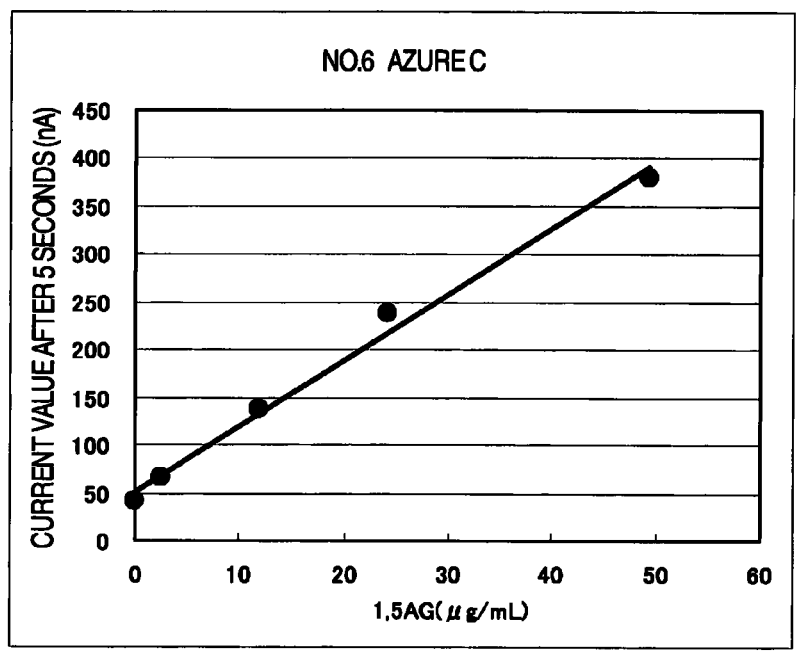
FIG. 10 is a calibration curve of Test No. 6 in Table 9 in Reference Example 10.
Figure 11:
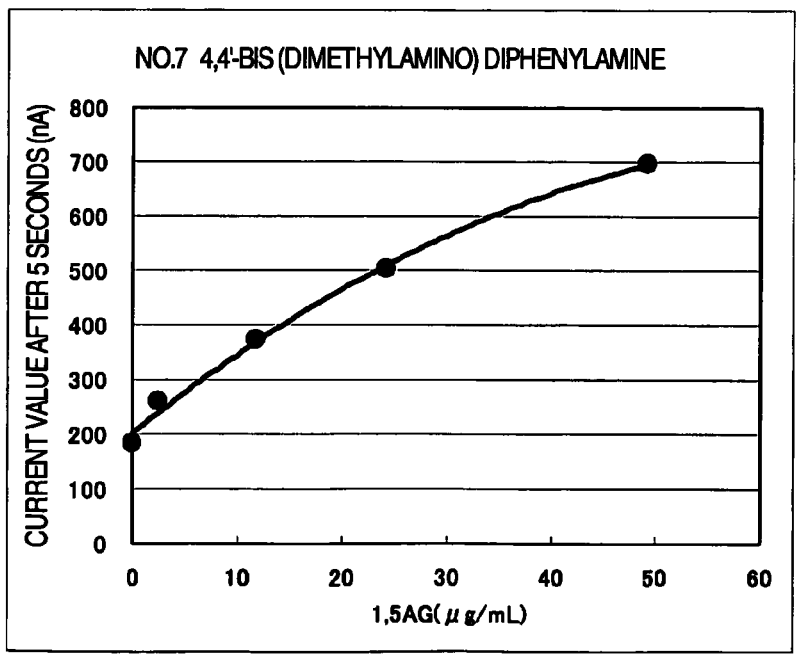
FIG. 11 is a calibration curve of Test No. 7 in Table 9 in Reference Example 10.
Figure 12:
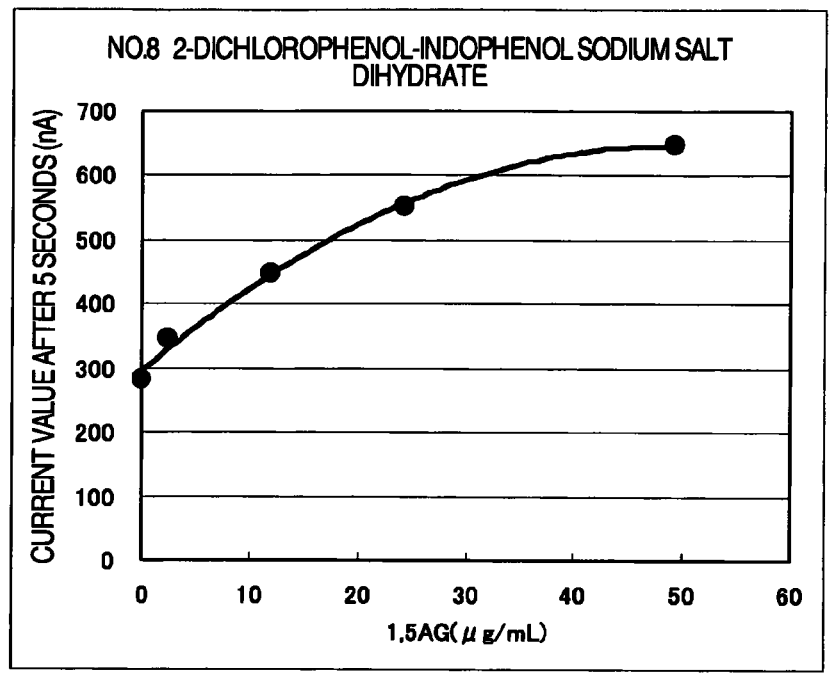
FIG. 12 is a calibration curve of Test No. 8 in Table 9 in Reference Example 10.
Figure 13:
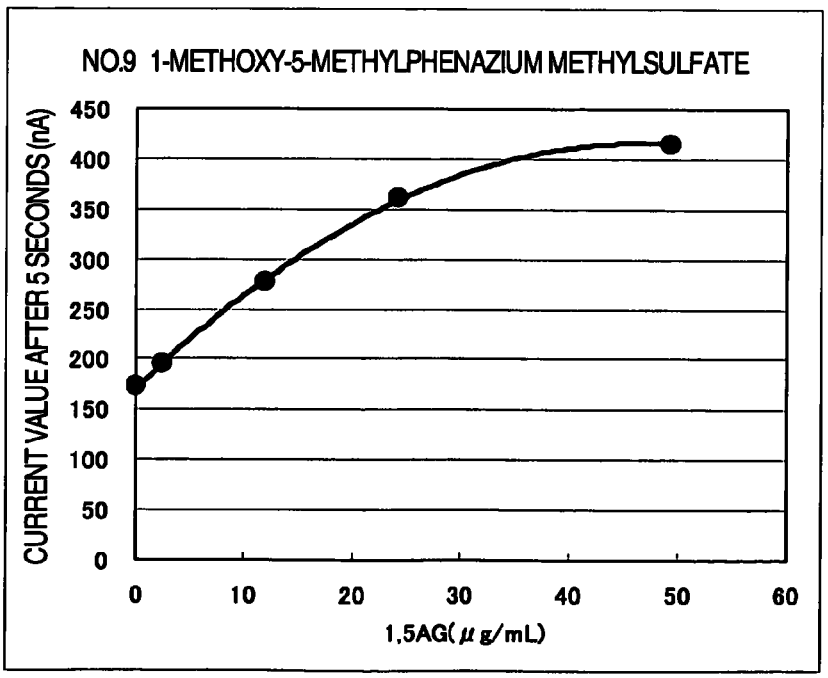
FIG. 13 is a calibration curve of Test No. 9 in Table 9 in Reference Example 10.
Figure 14:
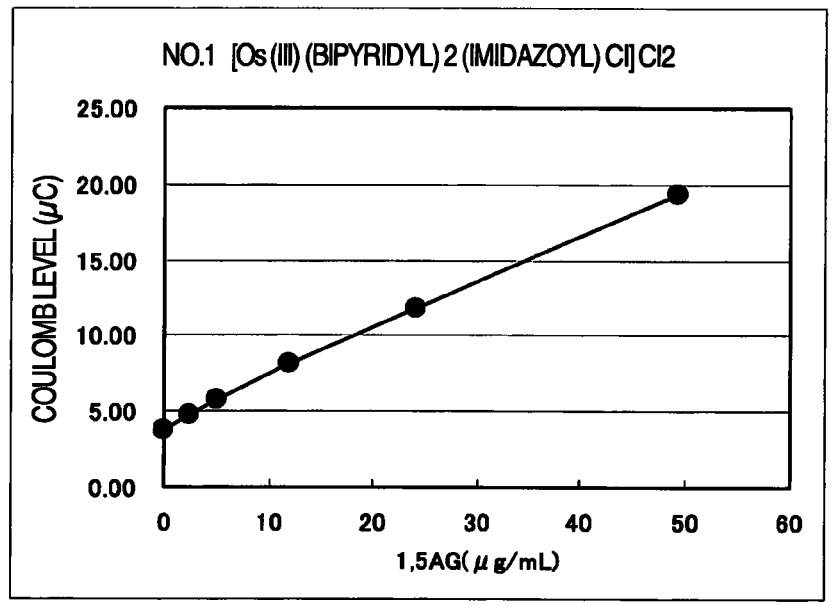
FIG. 14 is a calibration curve of Test No. 1 in Table 10 in Reference Example 11.
Figure 15:
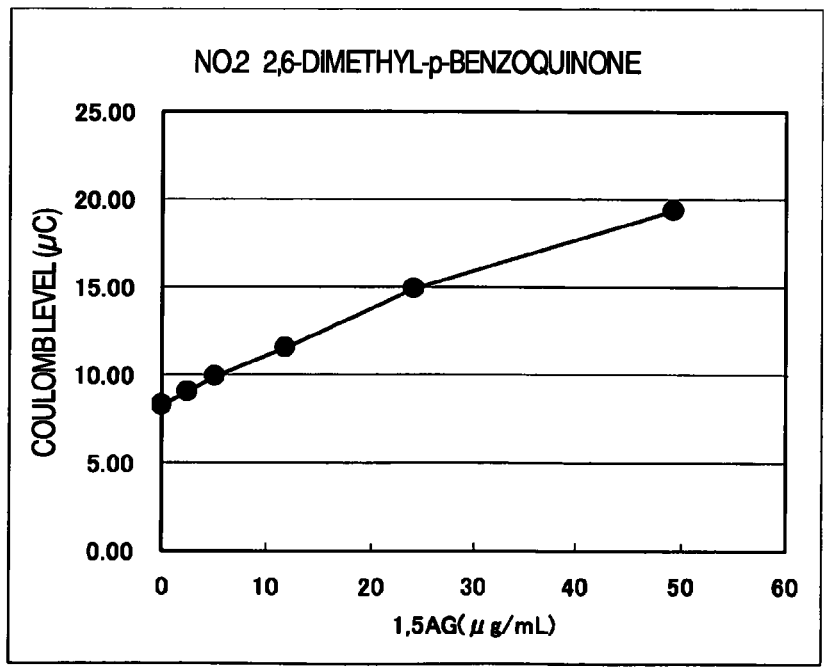
FIG. 15 is a calibration curve of Test No. 2 in Table 10 in Reference Example 11.
Figure 16:
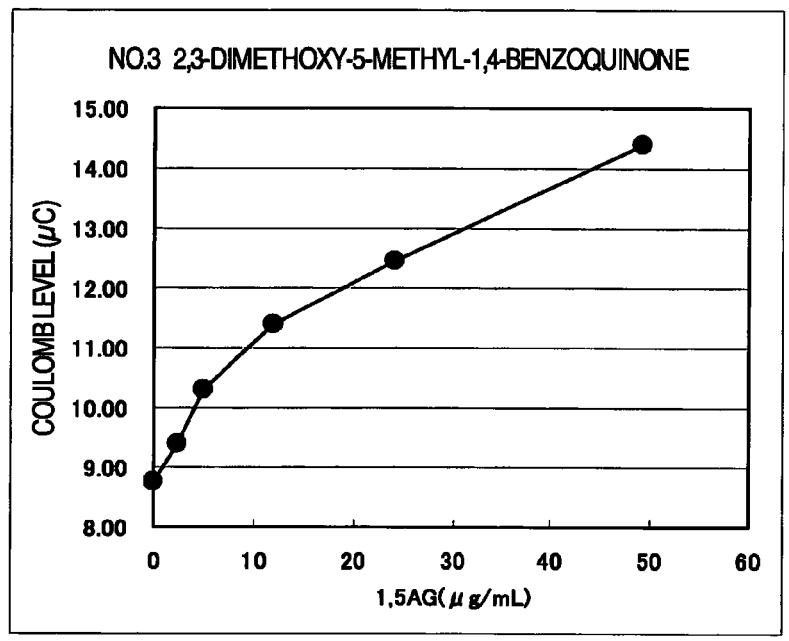
FIG. 16 is a calibration curve of Test No. 3 in Table 10 in Reference Example 11.
Figure 17:
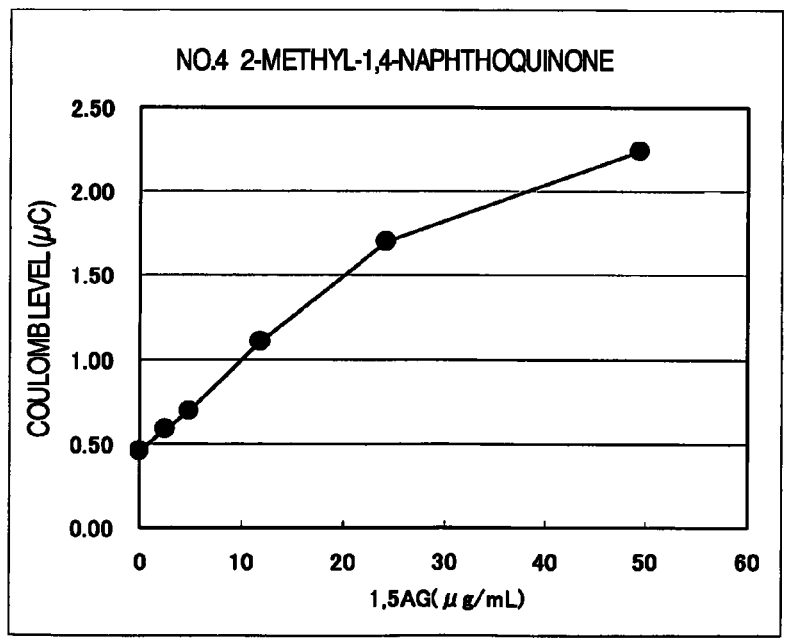
FIG. 17 is a calibration curve of Test No. 4 in Table 10 in Reference Example 11.
Figure 18:
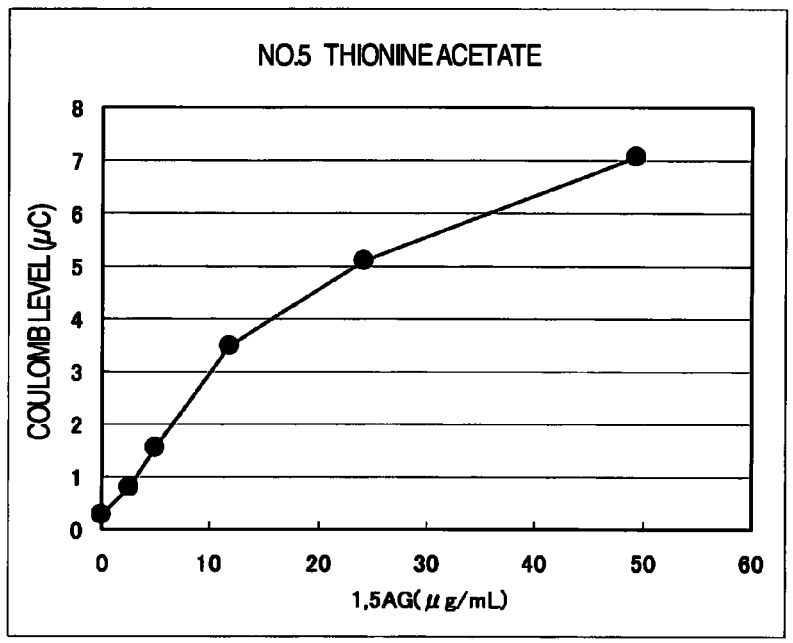
FIG. 18 is a calibration curve of Test No. 5 in Table 10 in Reference Example 11.
Figure 19:
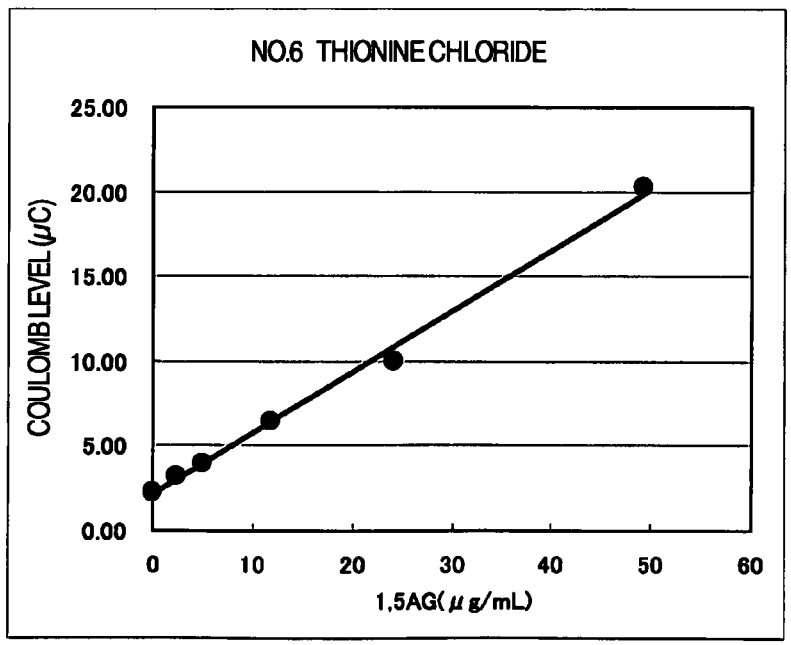
FIG. 19 is a calibration curve of Test No. 6 in Table 10 in Reference Example 11.
Figure 20:
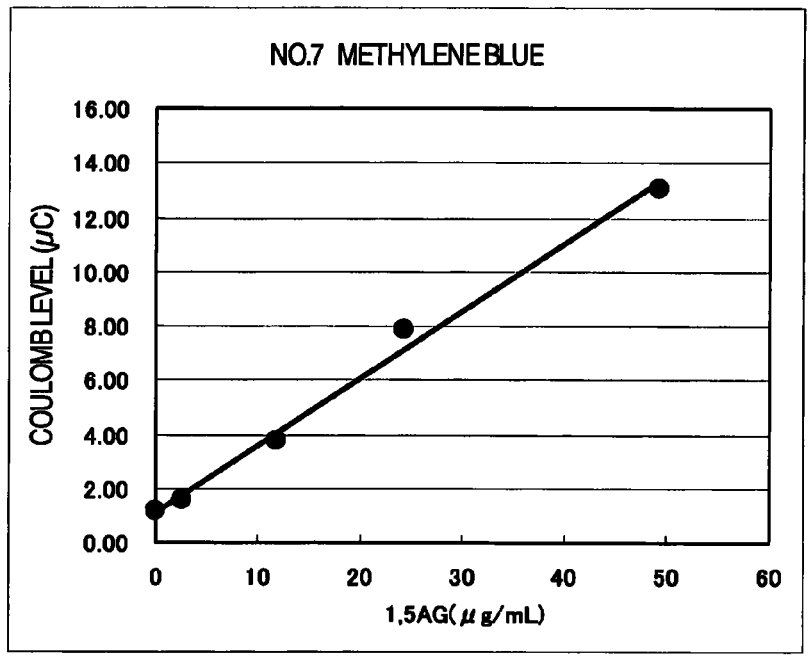
FIG. 20 is a calibration curve of Test No. 7 in Table 10 in Reference Example 11.
Figure 21:
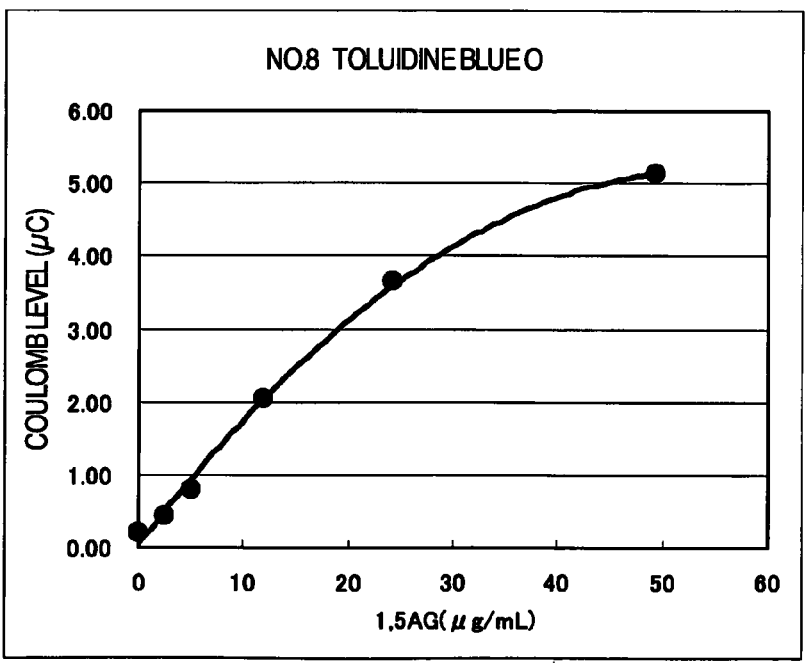
FIG. 21 is a calibration curve of Test No. 8 in Table 10 in Reference Example 11.
Figure 22:
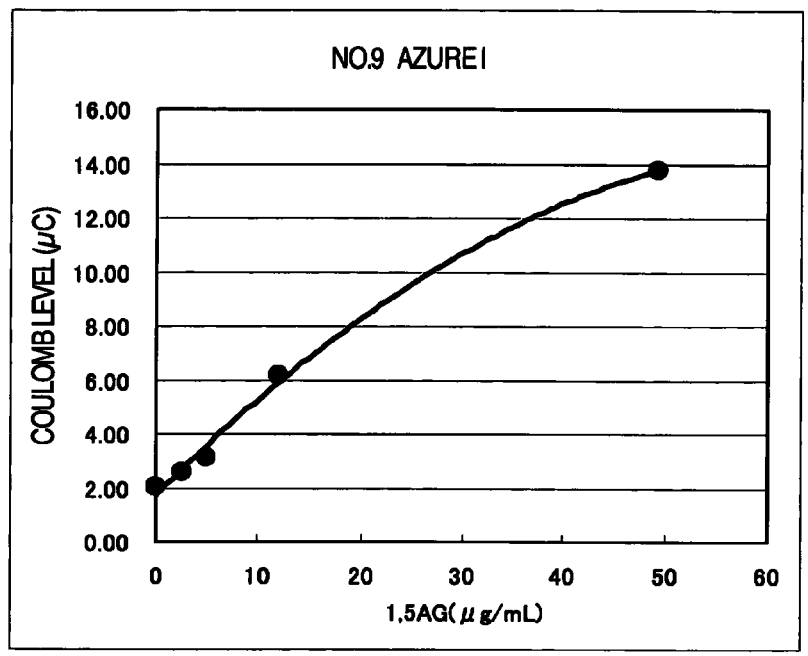
FIG. 22 is a calibration curve of Test No. 9 in Table 10 in Reference Example 11.
Figure 23:
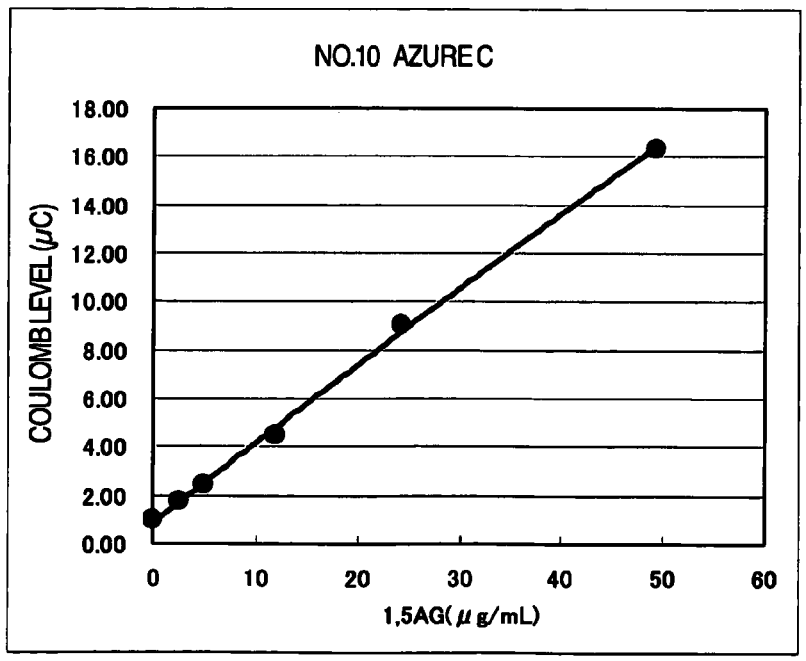
FIG. 23 is a calibration curve of Test No. 10 in Table 10 in Reference Example 11.
Figure 24:
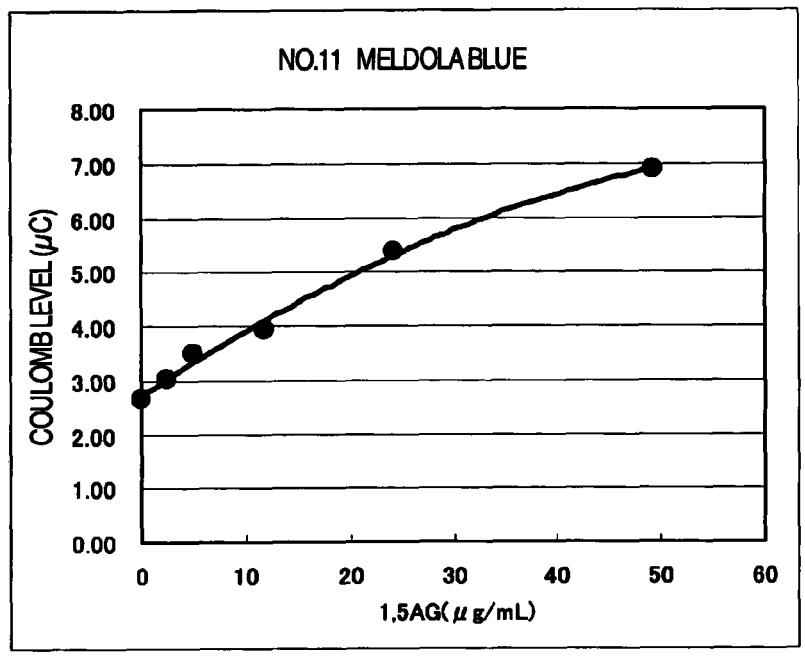
FIG. 24 is a calibration curve of Test No. 11 in Table 10 in Reference Example 11.
Figure 25:
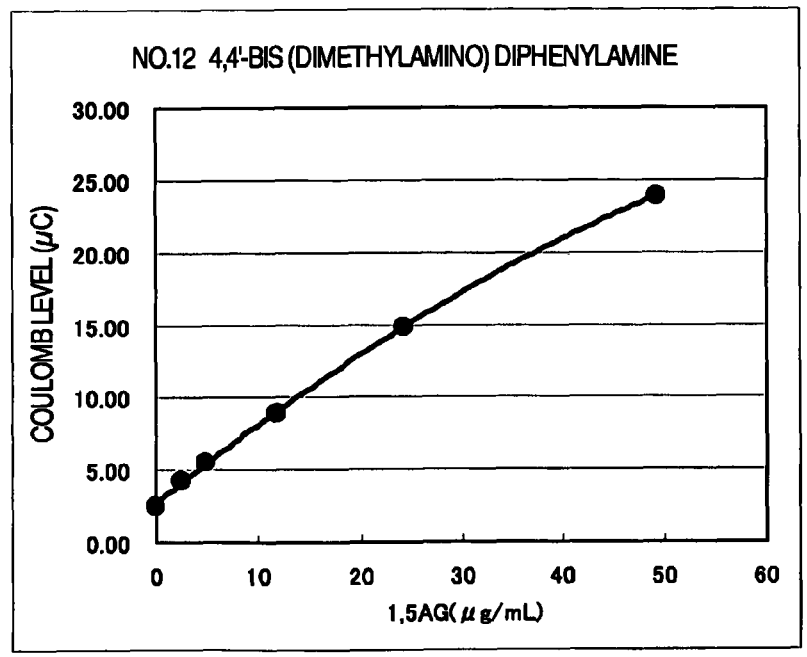
FIG. 25 is a calibration curve of Test No. 12 in Table 10 in Reference Example 11.
Figure 26:
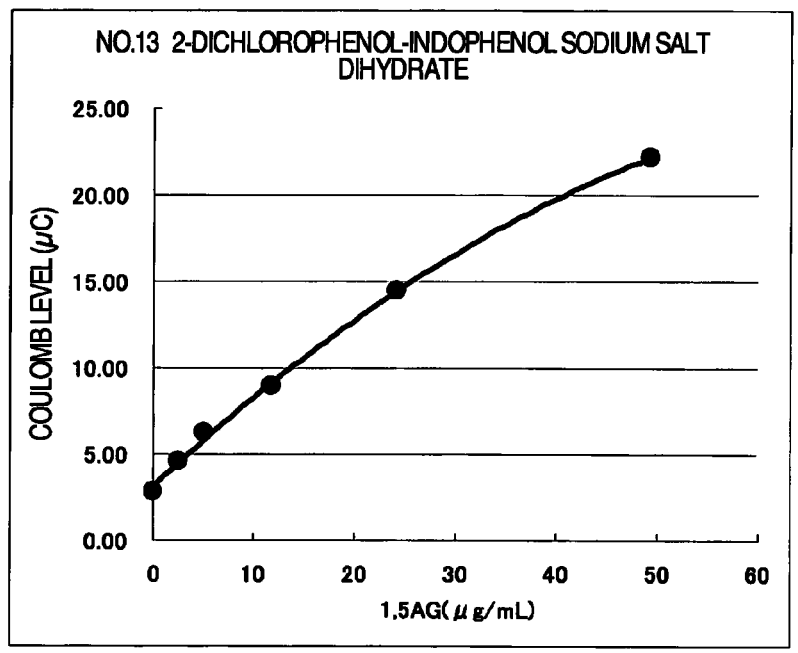
FIG. 26 is a calibration curve of Test No. 13 in Table 10 in Reference Example 11.
Figure 27:
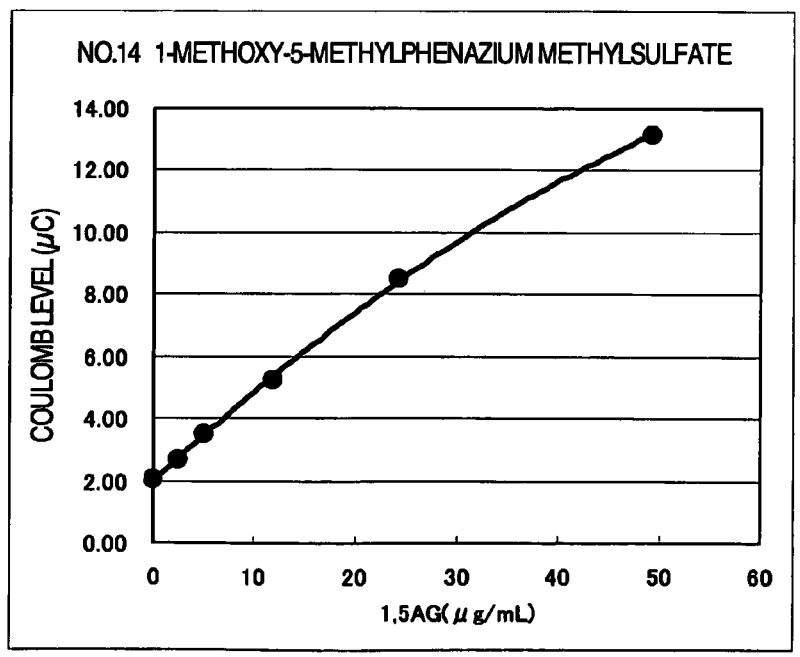
FIG. 27 is a calibration curve of Test No. 14 in Table 10 in Reference Example 11.
Figure 28:
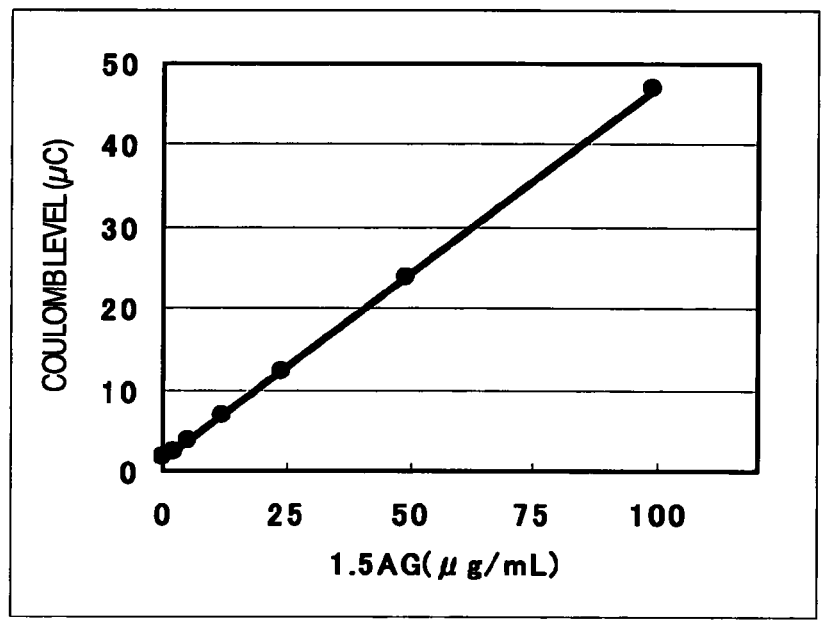
FIG. 28 is a calibration curve created in Example 6.
Figure 29:
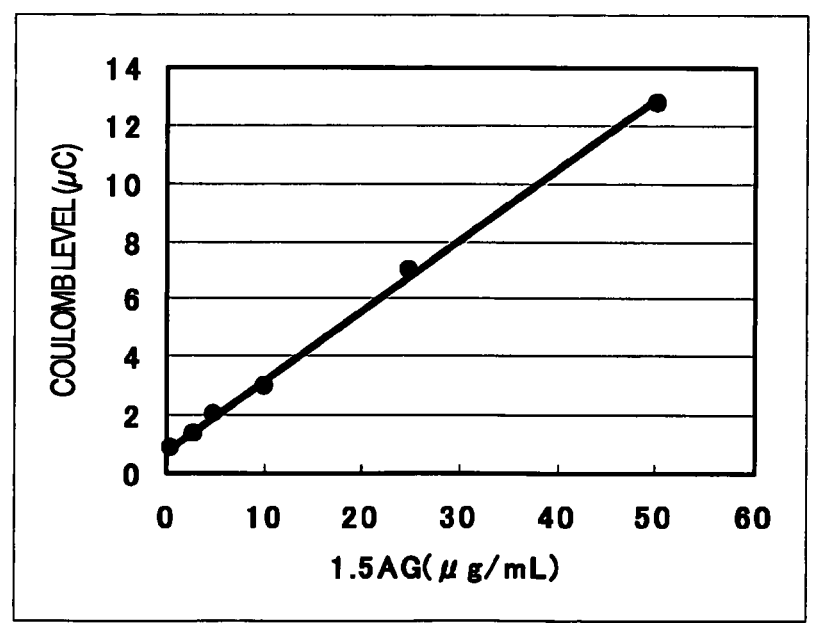
FIG. 29 is a calibration curve created in Example 7.
Figure 30:
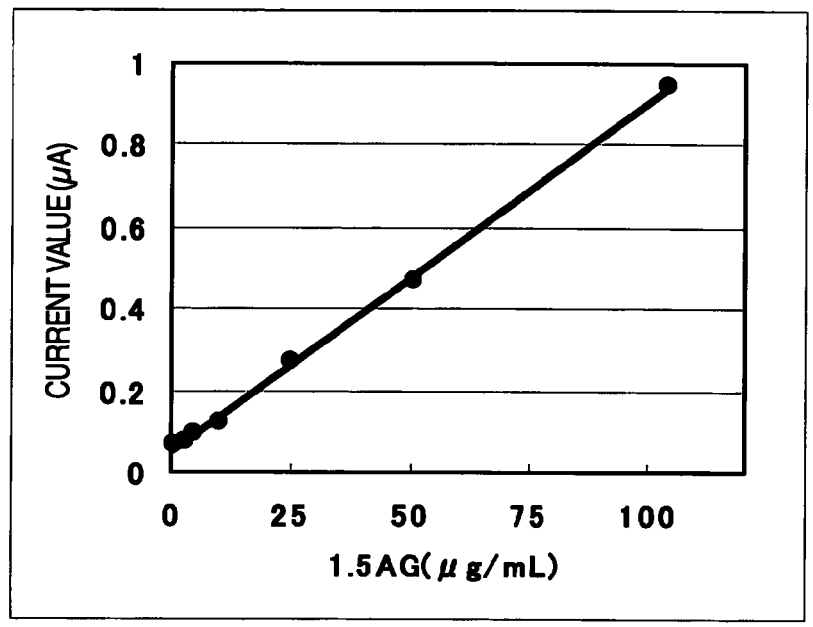
FIG. 30 is a calibration curve created in Example 8.
Figure 31:
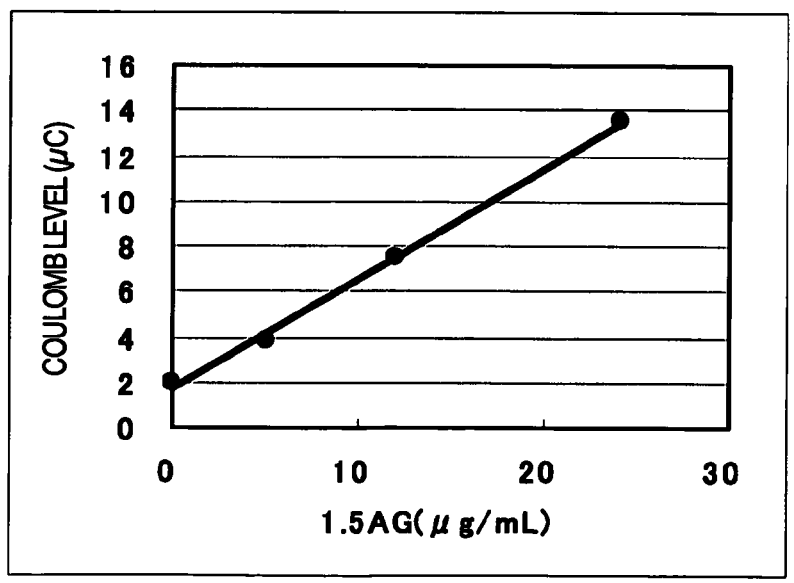
FIG. 31 is a calibration curve created in Example 9.
Figure 32:
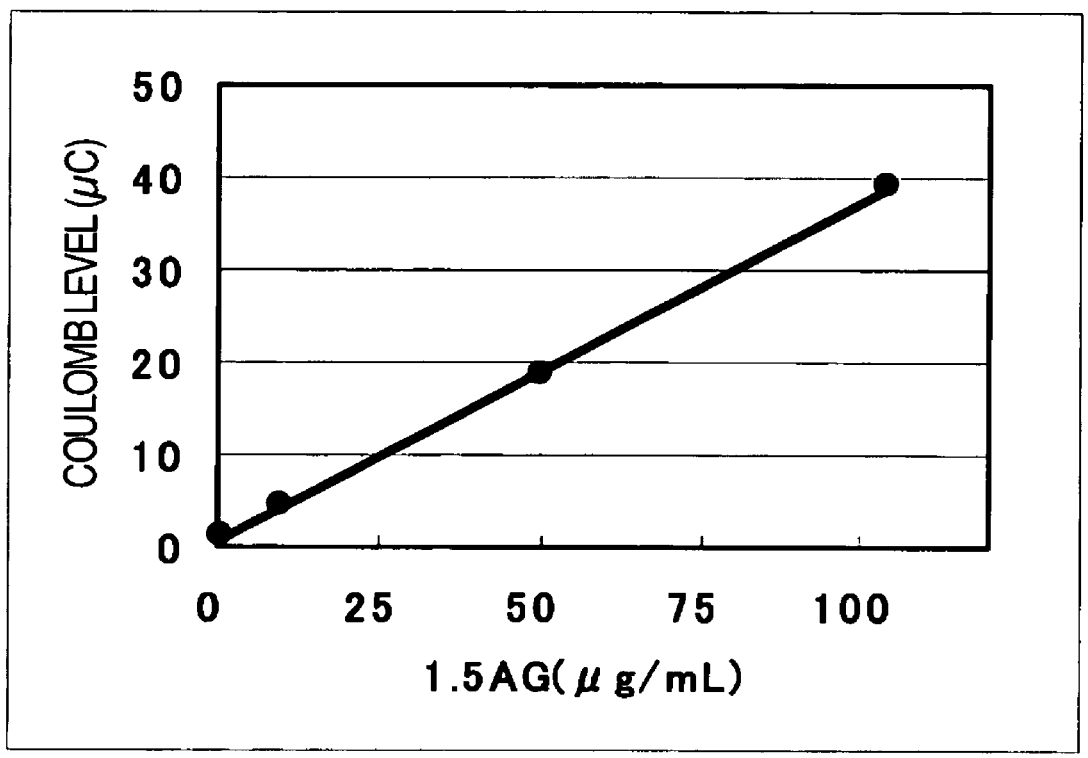
FIG. 32 is a calibration curve created in Example 10.

| 1. | Position at which specimen is applied |
| --- | --- |
| 2. | Support |
| 3. | Working electrode |
| 4. | Counter electrode |
| 5. | Resist |
| 6. | Reference electrode(carbon ink) |
| 6a. | Reference electrode(silver-silver chloride ink) |
| 11. | Electrode |
| 12. | Electrode |
| 13. | Electrode |

The invention claimed is:

1. A method for measuring 1,5-anhydroglucitol in whole blood, comprising the steps of (1) enzymatically converting glucose or a derivative thereof, or glucose and a derivative thereof, that interferes with the measurement of 1,5-anhydroglucitol, to a substance that an enzyme for measuring 1,5-anhydroglycitol does not react with; and (2) electrochemically measuring 1,5-anhydroglucitol with the enzyme and an electrode, in said whole blood from which blood cells have not been separated.

2. The method for measuring 1,5-anhydroglucitol according to claim 1, wherein the enzyme for measuring 1,5-anhydroglucitol is an oxidoreductase.

3. The method for measuring 1,5-anhydroglucitol according to claim 2, wherein the oxidoreductase is pyranose oxidase, L-sorbose oxidase, or 1,5-anhydroglucitol dehydrogenase.

4. The method for measuring 1,5-anhydroglucitol according to claim 3, wherein the oxidoreductase is derived from the genus *Pseudomonas* or *Agrobacterium*.

5. The method for measuring 1,5-anhydroglucitol according to any one of claims 1 to 4, wherein the 1,5-anhydroglucitol is electrochemically measured in the presence of a redox mediator.

6. The method for measuring 1,5-anhydroglucitol according to claim 5, wherein the redox mediator is an osmium complex, a quinone compound, a ferrocene compound, a phenothiazine compound, a phenoxazine compound, a phenazine compound, an indophenol compound, a diphenylamine compound, or a phenol compound.

7. The method for measuring 1,5-anhydroglucitol according to claim 1, wherein the 1,5-anhydroglucitol is electrochemically measured in the presence of a stabilizer.

8. The method for measuring 1,5-anhydroglucitol according to claim 7, wherein the stabilizer is 2-sulfobenzoic acid or 3-sulfobenzoic acid.

9. The method for measuring 1,5-anhydroglucitol according to claim 1, wherein the 1,5-anhydroglucitol is electrochemically measured by amperometry, coulometry, or cyclic voltammetry.

10. The method for measuring 1,5-anhydroglucitol according to claim 5, wherein the 1,5-anhydroglucitol is electrochemically measured using an electrode having a working electrode for measuring 1,5-anhydroglucitol that contains an oxidoreductase for measuring 1,5-anhydroglucitol and a redox mediator, and a counter electrode.

11. The method for measuring 1,5-anhydroglucitol according to claim 10, wherein the 1,5-anhydroglucitol is electrochemically measured using a differential electrode.

12. The method for measuring 1,5-anhydroglucitol according to claim 11, wherein the differential electrode is an electrode having a working electrode for measuring 1,5-anhydroglucitol that contains an oxidoreductase for measuring 1,5-anhydroglucitol and a redox mediator, a working electrode for measuring a blank that contains a redox mediator but does not contain an oxidoreductase for measuring 1,5-anhydroglucitol, and a counter electrode.

* * * * *